(12) United States Patent
Zhang et al.

(10) Patent No.: US 12,059,349 B2
(45) Date of Patent: Aug. 13, 2024

(54) HEART VALVE PROSTHESIS

(71) Applicant: JC Medical, Inc., Burlingame, CA (US)

(72) Inventors: Ji Zhang, Burnaby (CA); Brandon G. Walsh, Kaysville, UT (US); Cheng Yong Yang, Foster City, CA (US); Jinhua Zhu, San Francisco, CA (US)

(73) Assignee: JC Medical, Inc., Burlingame, CA (US)

( * ) Notice: Subject to any disclaimer, the term of this patent is extended or adjusted under 35 U.S.C. 154(b) by 243 days.

(21) Appl. No.: 17/545,998

(22) Filed: Dec. 8, 2021

(65) Prior Publication Data

US 2022/0096230 A1 Mar. 31, 2022

Related U.S. Application Data

(62) Division of application No. 16/240,408, filed on Jan. 4, 2019, now Pat. No. 11,253,363.

(60) Provisional application No. 62/781,537, filed on Dec. 18, 2018, provisional application No. 62/756,556, (Continued)

(51) Int. Cl.
*A61F 2/24* (2006.01)
*A61F 2/966* (2013.01)
*A61M 25/01* (2006.01)

(52) U.S. Cl.
CPC .......... *A61F 2/2436* (2013.01); *A61F 2/2412* (2013.01); *A61F 2/2415* (2013.01); *A61F 2/2418* (2013.01); *A61F 2/2463* (2013.01); *A61F 2/2433* (2013.01); *A61F 2/246* (2013.01); *A61F 2/966* (2013.01); *A61F 2002/9665* (2013.01); *A61M 25/0136* (2013.01)

(58) Field of Classification Search
CPC ........ A61F 2/24; A61F 2/2436; A61F 2/2412; A61F 2/2415; A61F 2/2418; A61F 2/2463; A61F 2/246; A61F 2/2433; A61F 2/966; A61F 2002/9665; A61B 2017/00783
See application file for complete search history.

(56) References Cited

U.S. PATENT DOCUMENTS

| 4,655,771 A | 4/1987 | Wallsten |
| 6,338,740 B1 | 1/2002 | Carpentier |
| 6,517,558 B2 | 2/2003 | Gittings et al. |

(Continued)

FOREIGN PATENT DOCUMENTS

| CN | 101919752 A | 12/2010 |
| CN | 102036622 A | 4/2011 |

(Continued)

OTHER PUBLICATIONS

PCT Written Opinion for PCT/US19/12406, published Jul. 2019, 17 pages.

*Primary Examiner* — Vi X Nguyen
(74) *Attorney, Agent, or Firm* — Morgan, Lewis & Bockius LLP

(57) ABSTRACT

A valve prosthesis can be manufactured by aligning a membrane along a support frame and attaching the membrane to the support frame. The membrane can have a plurality of first fibers arranged in a warp direction and a plurality of second fibers arranged in a weft direction that is transverse relative to the warp direction. The plurality of first fibers and the plurality of second fibers can be woven together. The warp and weft directions can be oriented oblique relative to a longitudinal axis of the support frame.

20 Claims, 10 Drawing Sheets

Related U.S. Application Data filed on Nov. 6, 2018, provisional application No. 62/614,489, filed on Jan. 7, 2018.

(56) References Cited

U.S. PATENT DOCUMENTS

| | | |
|---|---|---|
| 7,011,671 B2 | 3/2006 | Welch |
| 7,018,406 B2 | 3/2006 | Seguin et al. |
| 7,025,773 B2 | 4/2006 | Gittings et al. |
| 7,025,780 B2 | 4/2006 | Gabbay |
| 7,044,966 B2 | 5/2006 | Svanidze et al. |
| 7,070,616 B2 | 7/2006 | Majercak et al. |
| 7,347,869 B2 | 3/2008 | Hojeibane et al. |
| 7,387,640 B2 | 6/2008 | Cummings |
| 7,399,315 B2 | 7/2008 | Lobbi |
| 7,429,269 B2 | 9/2008 | Schwammenthal et al. |
| 7,510,572 B2 | 3/2009 | Gabbay |
| 7,621,948 B2 | 11/2009 | Herrmann et al. |
| 7,748,389 B2 | 7/2010 | Salahieh et al. |
| 7,789,909 B2 | 9/2010 | Andersen et al. |
| 7,803,185 B2 | 9/2010 | Gabbay |
| 7,824,443 B2 | 11/2010 | Salahieh et al. |
| 7,914,575 B2 | 3/2011 | Guyenot et al. |
| 7,947,075 B2 | 5/2011 | Goetz et al. |
| 7,959,666 B2 | 6/2011 | Salahieh et al. |
| 8,052,750 B2 | 11/2011 | Tuval et al. |
| 8,105,375 B2 | 1/2012 | Navia et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,353,953 B2 | 1/2013 | Giannetti et al. |
| 8,403,981 B2 | 3/2013 | Forster et al. |
| 8,414,643 B2 | 4/2013 | Tuval et al. |
| 8,540,767 B2 | 9/2013 | Zhang |
| 8,585,755 B2 | 11/2013 | Chau et al. |
| 8,585,756 B2 | 11/2013 | Chau et al. |
| 8,652,204 B2 | 2/2014 | Quill et al. |
| 8,657,872 B2 | 2/2014 | Seguin |
| 8,685,085 B2 | 4/2014 | Guyenot et al. |
| 8,728,155 B2 | 5/2014 | Montorfano et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,795,356 B2 | 8/2014 | Quadri et al. |
| 8,834,564 B2 | 9/2014 | Tuval et al. |
| 8,840,661 B2 | 9/2014 | Manasse |
| 8,870,950 B2 | 10/2014 | Hacohen |
| 8,876,894 B2 | 11/2014 | Tuval et al. |
| 8,876,895 B2 | 11/2014 | Tuval et al. |
| 8,951,299 B2 | 2/2015 | Paul et al. |
| 8,961,597 B2 | 2/2015 | Subramanian et al. |
| 8,992,604 B2 | 3/2015 | Gross et al. |
| 9,017,399 B2 | 4/2015 | Gross et al. |
| D732,666 S | 6/2015 | Nguyen |
| 9,050,188 B2 | 6/2015 | Schweich, Jr. et al. |
| 9,078,747 B2 | 7/2015 | Conklin |
| 9,132,009 B2 | 9/2015 | Hacohen et al. |
| 9,138,312 B2 | 9/2015 | Tuval et al. |
| 9,186,249 B2 | 11/2015 | Rolando et al. |
| 9,248,014 B2 | 2/2016 | Lane et al. |
| 9,277,993 B2 | 3/2016 | Gamarra et al. |
| 9,301,834 B2 | 4/2016 | Tuval et al. |
| 9,308,087 B2 | 4/2016 | Lane et al. |
| 9,339,378 B2 | 5/2016 | Quadri et al. |
| 9,339,386 B2 | 5/2016 | Guyenot et al. |
| 9,387,071 B2 | 7/2016 | Tuval et al. |
| 9,387,078 B2 | 7/2016 | Gross et al. |
| 9,393,114 B2 | 7/2016 | Sutton et al. |
| 9,421,094 B2 | 8/2016 | Schweich, Jr. et al. |
| 9,427,315 B2 | 8/2016 | Schweich, Jr. et al. |
| 9,433,500 B2 | 9/2016 | Chau et al. |
| 9,445,897 B2 | 9/2016 | Bishop et al. |
| 9,474,599 B2 | 10/2016 | Keranen |
| 9,486,313 B2 | 11/2016 | Stacchino et al. |
| 9,492,273 B2 | 11/2016 | Wallace et al. |
| 9,554,903 B2 | 1/2017 | Rowe et al. |
| 9,561,103 B2 | 2/2017 | Granada et al. |
| 9,572,665 B2 | 2/2017 | Lane et al. |
| 9,579,199 B2 | 2/2017 | Hauser et al. |
| 9,585,751 B2 | 3/2017 | Morriss et al. |
| 9,622,858 B2 | 4/2017 | Annest |
| 9,622,863 B2 | 4/2017 | Karapetian et al. |
| 9,629,716 B2 | 4/2017 | Seguin |
| 9,642,704 B2 | 5/2017 | Tuval et al. |
| 9,675,454 B2 | 6/2017 | Vidlund et al. |
| 9,750,605 B2 | 9/2017 | Ganesan et al. |
| 9,750,606 B2 | 9/2017 | Ganesan et al. |
| 9,763,657 B2 | 9/2017 | Hacohen et al. |
| 9,763,778 B2 | 9/2017 | Eidenschink et al. |
| 9,763,782 B2 | 9/2017 | Solem |
| 9,770,329 B2 | 9/2017 | Lane et al. |
| 9,782,256 B2 | 10/2017 | Zeng et al. |
| 9,788,931 B2 | 10/2017 | Giordano et al. |
| 9,788,941 B2 | 10/2017 | Hacohen |
| 9,801,715 B2 | 10/2017 | Kovalsky |
| D802,764 S | 11/2017 | Erzberger |
| 9,827,097 B2 | 11/2017 | Tuval et al. |
| 9,833,315 B2 | 12/2017 | Vidlund et al. |
| 9,861,473 B2 | 1/2018 | Lafontaine |
| 9,861,475 B2 | 1/2018 | Machold et al. |
| 9,861,479 B2 | 1/2018 | Conklin |
| 9,867,695 B2 | 1/2018 | Stacchino et al. |
| 9,907,652 B2 | 3/2018 | Chau et al. |
| 9,913,714 B2 | 3/2018 | Tuval et al. |
| 9,913,716 B2 | 3/2018 | Cartledge et al. |
| 9,918,835 B2 | 3/2018 | Guyenot et al. |
| 9,931,204 B2 | 4/2018 | Rothstein et al. |
| 9,956,075 B2 | 5/2018 | Salahieh et al. |
| 9,962,259 B2 | 5/2018 | Leo et al. |
| 9,974,647 B2 | 5/2018 | Ganesan et al. |
| 9,974,651 B2 | 5/2018 | Hariton et al. |
| 10,004,599 B2 | 6/2018 | Rabito et al. |
| 10,004,601 B2 | 6/2018 | Tuval et al. |
| 10,010,414 B2 | 7/2018 | Cooper et al. |
| 10,010,417 B2 | 7/2018 | Keidar |
| 10,034,747 B2 | 7/2018 | Harewood |
| 10,034,749 B2 | 7/2018 | Spence et al. |
| 10,052,199 B2 | 8/2018 | Spence et al. |
| 10,052,204 B2 | 8/2018 | McLean et al. |
| 10,064,718 B2 | 9/2018 | Keidar |
| 10,085,837 B2 | 10/2018 | Keidar et al. |
| 10,098,733 B2 | 10/2018 | Righini |
| D834,193 S | 11/2018 | Erzberger |
| 10,117,741 B2 | 11/2018 | Schweich, Jr. et al. |
| 10,130,468 B2 | 11/2018 | Rowe et al. |
| 10,143,550 B2 | 12/2018 | Achiluzzi |
| 10,143,552 B2 | 12/2018 | Wallace et al. |
| 10,149,759 B2 | 12/2018 | Naor |
| 10,179,042 B2 | 1/2019 | Braido et al. |
| 10,188,517 B2 | 1/2019 | Gainor et al. |
| 10,195,033 B2 | 2/2019 | Tuval et al. |
| 10,265,166 B2 | 4/2019 | Schweich, Jr. et al. |
| 10,265,172 B2 | 4/2019 | Krivoruchko |
| 10,278,820 B2 | 5/2019 | Bar et al. |
| 10,321,992 B2 | 6/2019 | Quill et al. |
| 10,327,899 B2 | 6/2019 | Sandstrom et al. |
| 10,350,062 B2 | 7/2019 | Peterson et al. |
| 10,363,133 B2 | 7/2019 | Lane et al. |
| 10,383,724 B2 | 8/2019 | Seguin |
| 10,413,408 B2 | 9/2019 | Krone et al. |
| 10,433,952 B2 | 10/2019 | Lane et al. |
| 10,433,961 B2 | 10/2019 | McLean |
| 10,449,039 B2 | 10/2019 | Ganesan et al. |
| 10,449,041 B2 | 10/2019 | Modine |
| 10,449,043 B2 | 10/2019 | Modine |
| D867,595 S | 11/2019 | Amer |
| 10,463,489 B2 | 11/2019 | Christianson et al. |
| 10,470,876 B2 | 11/2019 | Gurovich et al. |
| 10,512,456 B2 | 12/2019 | Hacohen et al. |
| 10,531,872 B2 | 1/2020 | Hacohen et al. |
| 10,543,077 B2 | 1/2020 | Tuval et al. |
| 10,543,081 B2 | 1/2020 | Naor et al. |
| 10,543,084 B2 | 1/2020 | Guyenot et al. |
| 10,555,808 B2 | 2/2020 | Wallace et al. |

(56) References Cited

U.S. PATENT DOCUMENTS

| | | |
|---|---|---|
| 10,555,812 B2 | 2/2020 | Duffy et al. |
| 10,575,951 B2 | 3/2020 | Johnson et al. |
| 10,583,002 B2 | 3/2020 | Lane et al. |
| 10,583,005 B2 | 3/2020 | Calomeni et al. |
| 10,617,520 B2 | 4/2020 | Rowe et al. |
| 10,624,740 B2 | 4/2020 | Perszyk |
| 10,631,977 B2 | 4/2020 | Tayeb et al. |
| 10,639,143 B2 | 5/2020 | Oba et al. |
| 10,646,333 B2 | 5/2020 | Rothstein |
| 10,646,340 B2 | 5/2020 | Manash et al. |
| 10,667,905 B2 | 6/2020 | Ekvall et al. |
| D899,653 S | 7/2020 | Erzberger |
| 10,716,668 B2 | 7/2020 | Quill |
| 10,729,541 B2 | 8/2020 | Francis et al. |
| 10,736,736 B2 | 8/2020 | Schweich, Jr. et al. |
| 10,743,988 B2 | 8/2020 | Seguin |
| 10,786,352 B2 | 9/2020 | Francis et al. |
| 10,799,343 B2 | 10/2020 | Rothstein et al. |
| 10,813,750 B2 | 10/2020 | Costello |
| 10,813,752 B2 | 10/2020 | Seguin |
| 10,813,757 B2 | 10/2020 | Cooper et al. |
| 10,828,150 B2 | 11/2020 | Tamir |
| 10,849,746 B2 | 12/2020 | Gregg et al. |
| 10,869,758 B2 | 12/2020 | Ganesan et al. |
| 10,898,325 B2 | 1/2021 | Calomeni et al. |
| D909,581 S | 2/2021 | Zeng |
| D910,852 S | 2/2021 | Zeng |
| 10,959,840 B2 | 3/2021 | Whitman |
| 10,966,824 B2 | 4/2021 | Zhang et al. |
| 10,966,829 B2 | 4/2021 | Poppe et al. |
| 10,973,634 B2 | 4/2021 | Cohen et al. |
| 11,007,057 B2 | 5/2021 | Pham et al. |
| 11,058,535 B2 | 7/2021 | Noe et al. |
| 2002/0032481 A1 | 3/2002 | Gabbay |
| 2003/0036791 A1 | 2/2003 | Bonhoeffer et al. |
| 2003/0040792 A1 | 2/2003 | Gabbay |
| 2003/0149478 A1 | 8/2003 | Figulla et al. |
| 2004/0260394 A1 | 12/2004 | Douk et al. |
| 2005/0075726 A1 | 4/2005 | Svanidze et al. |
| 2005/0137688 A1 | 6/2005 | Salahieh et al. |
| 2005/0137689 A1 | 6/2005 | Salahieh et al. |
| 2005/0251251 A1 | 11/2005 | Cribier |
| 2006/0173524 A1 | 8/2006 | Salahieh et al. |
| 2006/0217802 A1 | 9/2006 | Ruiz et al. |
| 2006/0259134 A1 | 11/2006 | Schwammenthal |
| 2006/0259135 A1 | 11/2006 | Navia et al. |
| 2007/0016286 A1 | 1/2007 | Herrmann et al. |
| 2007/0027533 A1 | 2/2007 | Douk |
| 2007/0027534 A1 | 2/2007 | Bergheim et al. |
| 2007/0100440 A1 | 5/2007 | Figulla et al. |
| 2007/0118210 A1* | 5/2007 | Pinchuk .................. A61L 27/34 623/1.26 |
| 2007/0244552 A1 | 10/2007 | Salahieh et al. |
| 2007/0250151 A1 | 10/2007 | Pereira |
| 2007/0250161 A1 | 10/2007 | Dolan |
| 2007/0260225 A1 | 11/2007 | Sakakine |
| 2008/0071361 A1 | 3/2008 | Tuval et al. |
| 2008/0071363 A1 | 3/2008 | Tuval et al. |
| 2008/0082166 A1 | 4/2008 | Styrc et al. |
| 2008/0177381 A1 | 7/2008 | Navia et al. |
| 2009/0043381 A1 | 2/2009 | Macoviak et al. |
| 2009/0054968 A1 | 2/2009 | Bonhoeffer et al. |
| 2009/0054976 A1 | 2/2009 | Tuval et al. |
| 2009/0132035 A1 | 5/2009 | Roth et al. |
| 2009/0192585 A1 | 7/2009 | Bloom et al. |
| 2009/0216310 A1 | 8/2009 | Straubinger et al. |
| 2009/0240320 A1 | 9/2009 | Tuval et al. |
| 2009/0275934 A1 | 11/2009 | Baxter |
| 2009/0287299 A1 | 11/2009 | Tabor et al. |
| 2010/0100167 A1 | 4/2010 | Bortlein |
| 2010/0249915 A1 | 9/2010 | Zhang |
| 2010/0249916 A1 | 9/2010 | Zhang |
| 2010/0249917 A1* | 9/2010 | Zhang .................. A61F 2/2427 623/2.11 |
| 2010/0256751 A1 | 10/2010 | Rowe et al. |
| 2010/0274088 A1 | 10/2010 | West et al. |
| 2010/0286768 A1 | 11/2010 | Alkhatib |
| 2011/0202128 A1 | 8/2011 | Duffy |
| 2011/0264202 A1 | 10/2011 | Murray, III |
| 2013/0172992 A1 | 7/2013 | Gross et al. |
| 2013/0211508 A1 | 8/2013 | Lane et al. |
| 2013/0231735 A1 | 9/2013 | Deem et al. |
| 2013/0261737 A1 | 10/2013 | Costello |
| 2014/0188211 A1 | 7/2014 | Roeder et al. |
| 2014/0228945 A1 | 8/2014 | Valdez et al. |
| 2015/0148893 A1 | 5/2015 | Braido |
| 2015/0148894 A1 | 5/2015 | Damm |
| 2015/0320556 A1 | 11/2015 | Levi |
| 2016/0015512 A1 | 1/2016 | Zhang et al. |
| 2016/0067040 A1 | 3/2016 | Agrawal et al. |
| 2016/0143732 A1 | 5/2016 | Glimsdale et al. |
| 2016/0262884 A1 | 9/2016 | Lombardi |
| 2017/0035569 A1 | 2/2017 | Deem et al. |
| 2017/0128203 A1 | 5/2017 | Zhang et al. |
| 2017/0165062 A1 | 6/2017 | Rothstein |
| 2017/0209268 A1 | 7/2017 | Cunningham et al. |
| 2018/0021129 A1 | 1/2018 | Peterson et al. |
| 2018/0025311 A1 | 1/2018 | Thomas |
| 2018/0338832 A1 | 11/2018 | Ganesan et al. |
| 2019/0000615 A1 | 1/2019 | Tayeb et al. |
| 2019/0015202 A1 | 1/2019 | Hacohen |
| 2019/0029854 A1 | 1/2019 | Calomeni et al. |
| 2020/0253731 A1 | 8/2020 | Manash |
| 2020/0397574 A1 | 12/2020 | Marchand et al. |
| 2021/0030540 A1 | 2/2021 | Marchand et al. |
| 2021/0038385 A1 | 2/2021 | Popp et al. |

FOREIGN PATENT DOCUMENTS

| | | |
|---|---|---|
| CN | 1013118630 A | 5/2013 |
| CN | 105263443 A | 1/2016 |
| CN | 105324091 A | 2/2016 |
| CN | 107405194 A | 11/2017 |
| DE | 102013224298 A1 | 5/2015 |
| EP | 2319458 | 4/2013 |
| EP | 2068767 | 7/2015 |
| EP | 2544626 | 10/2015 |
| EP | 2237746 | 5/2016 |
| EP | 2618779 | 8/2016 |
| EP | 3060173 | 8/2016 |
| EP | 2032080 | 5/2017 |
| EP | 3025682 | 5/2017 |
| EP | 3294221 | 3/2018 |
| EP | 3372199 | 9/2018 |
| EP | 3415119 | 12/2018 |
| JP | 2008-523922 | 7/2008 |
| JP | 2012-521854 | 9/2012 |
| JP | 2016-516492 | 6/2016 |
| WO | WO 2004/019825 | 3/2004 |
| WO | WO 2005/002466 | 1/2005 |
| WO | WO 2009/155561 | 12/2009 |
| WO | WO 2010/121076 | 10/2010 |
| WO | WO 2012/095455 | 7/2012 |
| WO | WO 2014/153152 | 9/2014 |
| WO | WO 2017/121194 | 7/2017 |
| WO | WO 2017/195125 | 11/2017 |
| WO | WO-2017/195125 A1 | 11/2017 |
| WO | WO 2018/055389 | 3/2018 |
| WO | WO 2018/099484 | 6/2018 |
| WO | WO 2018/187805 | 10/2018 |
| WO | WO 2018/217525 | 11/2018 |

\* cited by examiner

HEART VALVE PROSTHESIS

CROSS-REFERENCE TO RELATED APPLICATIONS

The present application is a divisional of U.S. application Ser. No. 16/240,408, filed on Jan. 4, 2019, which claims the benefit of and priority to U.S. Provisional Application No. 62/614,489, filed on Jan. 7, 2018, U.S. Provisional Application No. 62/756,556, filed on Nov. 6, 2018, and U.S. Provisional Application No. 62/781,537, filed on Dec. 18, 2018, the entireties of each of which are incorporated herein by reference.

TECHNICAL FIELD

The present disclosure relates to devices and methods for the percutaneous delivery and implantation of a cardiac valve prosthesis. The valve prosthesis can be delivered in a compressed state within a sheath to the defective native valve and released in situ.

BACKGROUND

Prosthetic heart valves are used to replace damaged or diseased heart valves. In vertebrate animals, the heart is a muscular organ with four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is more common since they reside in the left side of the heart where pressures are the greatest.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open-heart surgery is particularly invasive and involves a lengthy and difficult recovery period.

The foregoing examples of the related art and limitations related therewith are intended to be illustrative and not exclusive. Other limitations of the related art will become apparent to those of skill in the art upon a reading of the specification and a study of the drawings.

SUMMARY

The present disclosure relates to heart valve prostheses, delivery devices, and actuation handles that can facilitate delivery of a heart valve prosthesis to a defective native valve structure in a patient, such as the aortic valve. In some embodiments, the delivery can be performed using a transcatheter approach.

The delivery devices and actuation handles can enable a clinician to more easily maneuver and advance the delivery device through blood vessels leading to the heart, as well as through tortuosities of such vessels, using a transvascular approach, such as a transfemoral approach. Indeed, some embodiments disclosed herein enable components of the heart valve prosthesis to be advanced in tandem, as an axially displaced unit (with or without partial or full overlapping between the components), while still being movably connected, movably attached, flexibly connected, displaceably connected, linked, or coupled to each other, thereby minimizing a passing profile or cross section of the delivery device. Optionally, the distance from which the components of the heart valve prosthesis may be serially displaced may be variable, such that various components are adjacent or potentially inches or feet away. Further, the interconnection of components of the heart valve prosthesis can allow different degrees of motion and can be set into an engaged or retained position that provides a limited range of motion. In some embodiments, the engaged position can also provide a preset relative positioning of the components of the heart valve prosthesis to facilitate proper placement and release of the heart valve prosthesis. Additionally, some embodiments can provide a clinician with a high degree of control and enhance the maneuverability of the heart valve prosthesis when implanting the heart valve prosthesis at the target location.

In accordance with some embodiments, a procedure is provided for a transcatheter aortic valve implantation (TAVI) and/or a transcatheter aortic valve replacement (TAVR). For example, in the TAVI procedure, a clinician can anchor the anchoring component of the heart valve prosthesis relative to the aortic valve annulus to guide the placement of the prosthetic leaflet structure. The valve prosthesis can comprise prosthetic leaflets, an anchoring component, a valve frame component, and a tethering component, which allows the anchoring component and the frame component to be placed serially in a delivery device in order to reduce the overall crossing profile of the delivery device. The tethering component can be coupled to the anchoring component and the frame component to permit a range of motion and in some embodiments, to restrict other motion. The tethering component can be slidable relative to the anchoring component between a released position and a retained position. In the retained position, the tethering component can allow relative movement of the valve frame component and a preset or predetermined position which the valve frame component is optimally located relative to the anchoring component, which can facilitate placement and release of the valve prosthesis.

For example, in some embodiments, the interconnection can be implemented using a novel approach of looping the tethering component around "U-shaped" members of the anchoring component. The tethering component can slide along the anchoring component until reaching the end of the travel on the anchoring component. The clinician can exert tension on the tethering component until the tethering component is seated in the engagement area. This action can ratchet the tethering component and engage it to the engagement area of the anchoring component. Thereafter, the tethering component establishes a fixed range of longitudinal travel of the valve frame component relative to the anchoring component, and subsequently a proper position of the valve frame component in the anatomy, based only on the clinician placing the anchoring component into the aortic sinus region (the clinician can see under fluoroscopy and can "feel" the placement).

Thus, some embodiments disclosed herein advantageously provide a delivery device that has a reduced passing profile or cross section, thereby enabling delivery of a heart valve prosthesis in a safer, less invasive manner than traditional approaches. As such, open-heart surgery can be avoided because the heart valve prosthesis can be advanced to the heart using a catheter via an access point in the blood vessel, such as the femoral artery. This provides enormous benefits to patients, including less trauma to the patient, greater ease of recovery, and potentially fewer surgical risks, to name a few.

Further, although the in-series arrangement of the anchoring component and the valve frame component overcomes the challenge of creating a low-profile delivery device, the advantageous arrangement of the interconnection overcomes yet another critical challenge: how to optimally position the valve prosthesis within the native valve structure and to reliably anchor it in place. Indeed, some embodiments disclosed herein address this challenge and teach structures and methods for using a tethering component to operatively couple the anchoring component to the valve frame component in a delivery device.

The delivery device can comprise a proximal sheath that can house at least a portion of the anchoring component and a distal carrier assembly that can house at least a portion of the valve frame component. The tethering component can extend between the anchoring component and the valve frame component when the valve prosthesis is loaded onto the delivery device. The valve prosthesis can be released from the delivery device in a component-by-component manner that allows the clinician to maneuver and position the anchoring component first, followed by the valve frame component.

In some embodiments, the anchoring component can be coupled to an engagement member or grasper of the delivery device that allows the clinician to push or pull the anchoring component. The grasper can be released from engagement with the anchoring component when the anchoring component is properly seated relative to the native valve annulus.

In addition, in some embodiments, the distal carrier assembly of the delivery device can comprise two components or be referred to as a two-part nose cone assembly. In accordance with some embodiments is the realization that if a single tubular member or nose cone is used to sheath most of the valve frame component, various problems can arise due to the expansive force and corresponding compressive force required to maintain the valve frame component in its compressed configuration during delivery to a target valve structure. Because the delivery device can be quite long (for example, in some embodiments, up to about 4 to 6 feet or more, although the length can be less than 4, 3, or 2 feet), these forces can create a much stiffer distal section of the delivery device. Further, these forces can require a high degree of longitudinal force to release the valve frame component due to the high frictional forces due to the radial force of the valve implant.

Thus, the radial and frictional forces of such configurations can cause problems of matching handle actuation and make precise positioning of the distal end of the delivery device quite difficult. For example, the friction tends to be a variable friction that makes it difficult for a clinician to position the components of the valve prosthesis relative to each other, which can lead to unpredictable and/or imprecise component positioning or deployment. Thus, some embodiments herein include the realization that by separating the distal carrier or nose cone assembly into two components (such as a proximal and distal enclosure), the components can cover less surface area of the valve frame component, thus reducing the radial forces exerted on a single component and the resultant friction that would need to be overcome in order to actuate or release the valve frame component. As such, the problems associated with a single tubular member are much more manageable.

Additionally, in some embodiments, a two-part distal carrier assembly can also enable the clinician to release the valve frame component in an advantageous sequence. For example, during testing and development of the valve prostheses, deployment systems, and handle actuators disclosed herein, some embodiments demonstrate advantageous characteristics by permitting a distal end portion of the valve frame component to open first, before a proximal end portion of the valve frame component is released. In some embodiments, the valve frame component can have one or more anchors at its distal end portion that can supplement the outward expansive force (due to self-expansion of the valve frame component) and its resultant frictional engagement. By opening the distal end portion first (by actuation of distal nose cone or enclosure), the distal end portion can "flower" out and engage with the native valve structure to secure a longitudinal position of the valve frame component relative to the native valve structure. Thereafter, the self-expanding radial outward force of the valve frame component can cause the proximal end portion of the valve frame component to become disengaged and released from the proximal nose cone or enclosure.

Some embodiments can also provide self-aligning features to allow the components of the delivery assembly to be moved from a releasing state (where the components of the valve prosthesis are released from engagement with the delivery assembly) to a nested or stowed state in which outer surfaces of portions of the delivery assembly are aligned or in an abutting position at a seam. This alignment, abutment, or positioning can provide a smoother outer profile that can reduce the likelihood of having the delivery assembly snag or become entangled with the prosthetic valve after being released or with other vasculature as the delivery assembly is retrieved from the patient's vasculature.

For example, in some embodiments, the distal carrier or nose cone assembly can include an internal plunger or piston mechanism. The plunger mechanism can be compressed when the valve frame component is loaded into the delivery device. As the valve frame component is released, a spring of the plunger mechanism can push a plunger head to a predetermined position relative to the distal carrier assembly. In accordance with some embodiments, in the predetermined position, the plunger head can be exposed partially from the distal enclosure and be configured to engage with the proximal enclosure to align the proximal and distal enclosures relative to each other in an abutting relationship. The plunger head can therefore engage with both the proximal and distal enclosures to reduce the likelihood of catching or snagging of the delivery device with the prosthetic valve or other vasculature during retrieval of the delivery device. Additionally, such features can also aid in proximal retraction of the delivery device into an introducer sheath. Moreover, the plunger head can also provide a proximal surface that can be in contact with the distal end portion of the valve frame component and not catch or snag with the intricate mesh of the valve frame component, thereby ensuring that the valve frame component can flower open without catching on the delivery device. Accordingly, some embodiments can include one or more of these advantageous features that address the problem of having the valve prosthesis and/or the delivery device catch or snag on each other or surrounding anatomy.

Furthermore, due to the reduced cross-sectional profile of the delivery device, retrograde delivery of a valve prosthesis through the blood vessel (such as femoral artery in a transfemoral retrograde approach) can be possible with reduced risk of trauma to the surrounding vasculature. For example, retrograde delivery of the valve prosthesis through the femoral artery has been associated with aortofemoral artery injury and/or rupture, and carries a potential risk of stroke as the delivery involves crossing the aortic arch. However, the various features and advantages achieved using some embodiments disclosed herein provide a valve prosthesis and delivery device that minimizes damage along the delivery path of device while also minimizing the invasive nature of the implantation procedure.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded or omitted from any embodiment of the present disclosure. Additional aspects and advantages of the present disclosure are set forth in the following description and claims, particularly when considered in conjunction with the accompanying examples and drawings.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Certain features of valve prostheses, delivery devices, actuation handles, other devices, systems, and methods which can be implemented with the valve prostheses, delivery devices, actuation handles, other devices, systems, and methods discussed in the present disclosure, can implement features of and/or be used in combination with other features of valve prostheses, delivery devices, actuation handles, other devices, systems, and methods described for example in International Application No. PCT/US2019/012406, entitled HEART VALVE PROSTHESIS AND DELIVERY, filed on Jan. 4, 2019, by Ji Zhang, Brandon G. Walsh, Cheng Yong Yang, Jinhua Zhu, and Dennis Michael McMahon, and in International Application No. PCT/US2019/012408, entitled PROSTHETIC HEART VALVE DELIVERY SYSTEM, filed on Jan. 4, 2019, by Ji Zhang, Brandon G. Walsh, and Cheng Yong Yang, the entirety of each of which is incorporated herein by reference.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
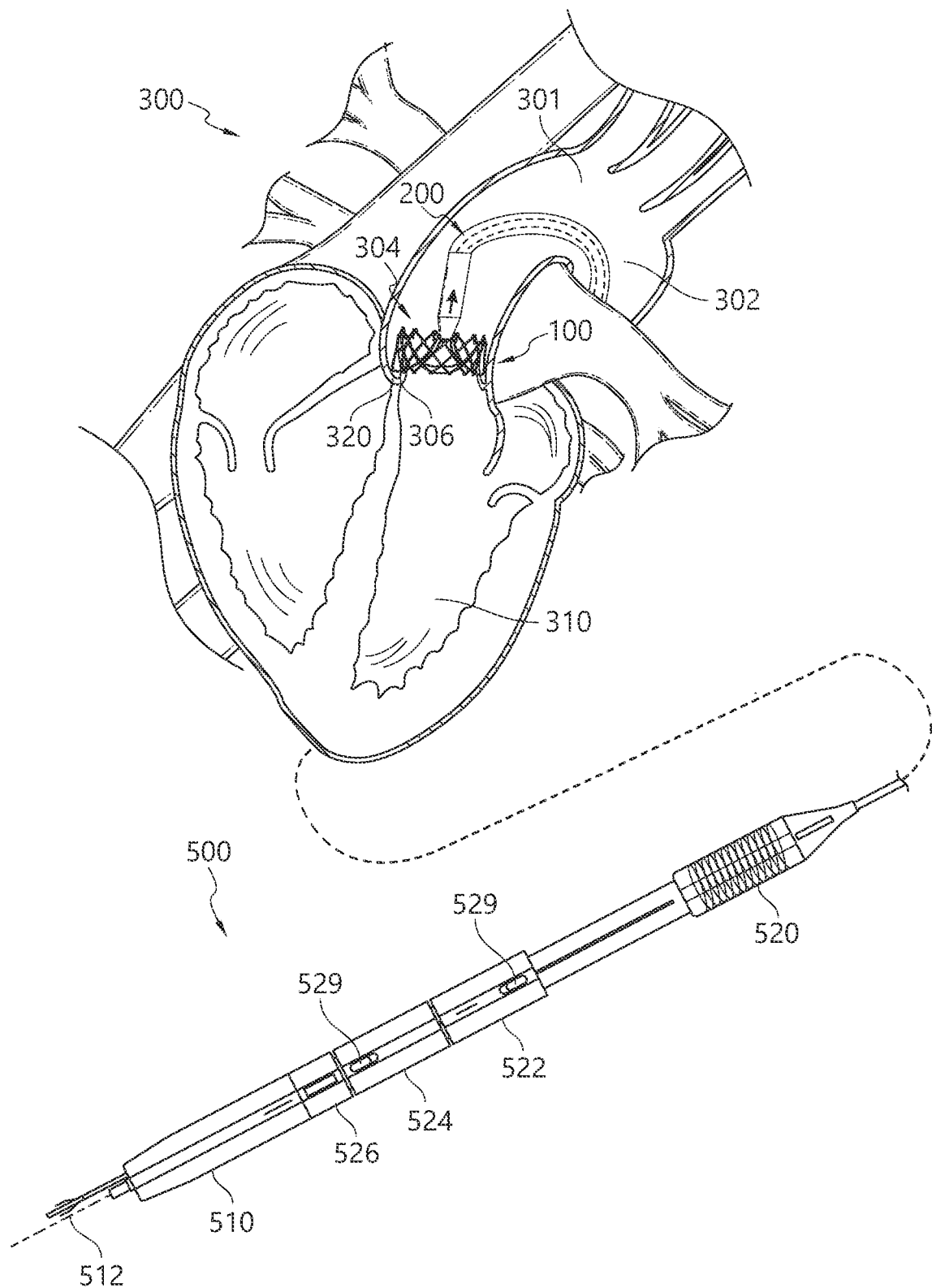
FIG. 1 illustrates delivery of a valve prosthesis using a valve delivery device in a transfemoral retrograde approach, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present disclosure sets forth specific details of various embodiments, it will be appreciated that the description is illustrative only and should not be construed in any way as limiting. Additionally, it is contemplated that although particular embodiments of the present disclosure may be disclosed or shown in the context of aortic valve prostheses, such embodiments may be used in other cardiac valve prosthesis applications. Furthermore, various applications of such embodiments and modifications thereto, which may occur to those who are skilled in the art, are also encompassed by the general concepts described herein.

Various embodiments will now be described more fully hereinafter. Such embodiments may, however, be embodied in many different forms and should not be construed as limited to the embodiments set forth herein; rather, these embodiments are provided so that this disclosure will be thorough and complete, and will fully convey its scope to those skilled in the art. Thus, one or more features shown or otherwise disclosed in an embodiment herein may be interchangeably used or incorporated into another embodiment that may not expressly show or disclose such feature(s). Further, one or more features shown or otherwise disclosed for an embodiment herein may be excluded from such embodiment, unless expressly indicated, using skill in the art.

As with all cardiac valves, a healthy aortic valve will open to allow blood flow and close to prevent backflow of blood. However, disease and dysfunction of the valve can result in regurgitation or decreased blood flow (stenosis). In such cases, a replacement aortic valve prosthesis must be used to perform the functions of a healthy aortic valve.

Minimally invasive surgical techniques are evolving, where a valve prosthesis can be introduced into a patient using a catheter that is introduced via a small incision that provides access to, for example, a femoral artery or directly to the heart. These implantation techniques have shown promising results in providing treatment options for patients who are poor open surgical candidates. Nevertheless, challenges still remain in such catheter-based delivery of prosthetic valves.

For example, in according with an aspect of at least one embodiment disclosed herein is the realization that advancing a conventional tubular delivery device through a vessel exerts stress against the vessel walls and carries the risk of damaging the vessel walls. Further, in according with an aspect of at least one embodiment disclosed herein is the realization that transcatheter prosthetic valves may not be able to treat patients with aortic regurgitation. Additionally, in according with an aspect of at least one embodiment disclosed herein is the realization that conventional prosthetic valves may be difficult to position, may require rapid ventricular pacing, and may have limited expansion. Accordingly, implantation and use of conventional prosthetic valves may result in complications, such as vascular damage, moderate to severe paravalvular leakage, valve thrombosis/migration, coronary artery blockage, and excessive stress due to excessive radial force.

The present disclosure describes various aspects of heart valve prostheses that can be delivered to a defective heart valve in a patient. The valve prostheses can comprise at least one valve anchor or clasper, which is movably connected, movably attached, flexibly connected, displaceably connected, linked, or coupled to a radially-expandable valve support or frame. The valve frame can comprise prosthetic valve leaflets or cusps and provide the functionality of the native heart valve. Certain features of valve prostheses, which can be implemented with the prostheses discussed in the present disclosure, are also further described for example, in U.S. Pat. No. 8,366,768, the entirety of which is incorporated herein by reference.

Thus, the present disclosure provides a variety of features that can be optionally incorporated or excluded from any of the embodiments explicitly discussed or illustrated herein. These modifications and combinations of features can be performed by a person of skill to achieve advantages and benefits discussed herein. Further, certain modifications or combinations are indicated or suggested herein, but it is contemplated that a person skill can implement or exclude certain aspects or features disclosed herein in developing a suitable embodiment or implementation of these teachings. Advantageously, various embodiments described herein allow for treating patients with aortic regurgitation, permit precise axial, angular, and radial positioning of the valve prosthesis, minimize valve migration and paravalvular leakage while avoiding damage to the valve annulus, minimize the need for a pacemaker, and decrease the likelihood of blocking the coronary artery.

Some of these features and benefits of the heart valve prosthesis are illustrated with respect to FIGS. 1-5. FIG. 1 illustrates the use of the delivery device 200 in a human heart 300. The heart 300 can comprise an aorta 301 having an aortic arch 302 and an aortic valve 304. The aorta valve 304 can comprise a plurality of native valve leaflets 306 and separate the aorta 301 from the left ventricle 310. In accordance with some embodiments, the delivery device 200 can be advanced retrograde through the aorta 301 until reaching and being positioned through the native valve leaflets 306 of the aortic valve 304.

Figure 2:
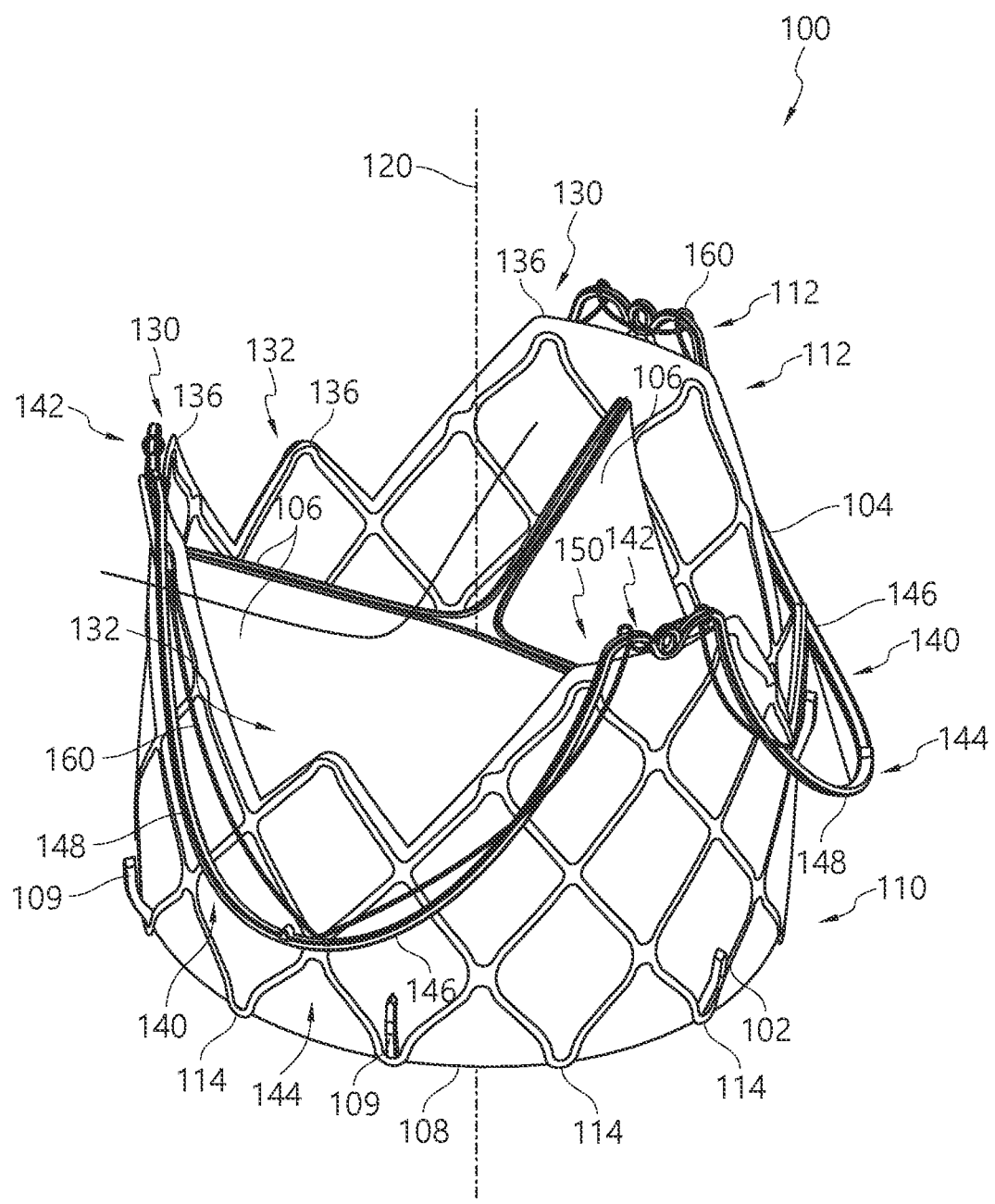
FIG. 2 shows a valve prosthesis, according to some embodiments.

With reference to FIGS. 1 and 2, during delivery of the valve prosthesis 100 to the native valve site, the valve anchor 104 and the support frame 102 can be positioned in tandem, as an axially displaced unit (with or without partial or full overlapping between the anchor and the frame) along the longitudinal axis of the delivery device 200. This configuration, as opposed to a concentric arrangement, can allow a more radially compact configuration of the components of the valve prosthesis 100, creating a much smaller cross-section and facilitating a catheter-based delivery. This can improve the flexibility of the delivery device 200, enabling the delivery device 200 to be advanced over a guidewire through the tortuous geometries of the circulatory system, and in particular, the aortic arch 302. Indeed, even with guidewire-directed delivery devices, the aortic arch 302 represents a difficult obstacle due to its sudden and high-degree of curvature. Often, this is a limiting constraint for some surgeries or delivery devices. However, in accordance with the various benefits and advantages of some embodiments disclosed herein, as illustrated in FIG. 1, the delivery device 200 can be advanced over the aortic arch 302 to a target location in the region of the aortic valve 304.

As shown in FIG. 1, once the valve anchor 104 is in the desired position, the support frame 102 can be released from the distal carrier assembly and expanded into apposition with the native valve leaflets 306 and the internal aspects of the valve anchor 104, thus sandwiching the native valve leaflets 306 between the support frame 102 and the valve anchor 104. Advantageously, by sandwiching the native valve leaflets 306 between the support frame and the valve anchor, the valve prosthesis 100 can have reduced reliance on radial force retention. Further, by sandwiching the native valve leaflets 306 between the support frame and the valve anchor, the likelihood of the native valve leaflets 306 blocking the opening of the coronary artery is reduced, which may be beneficial for patients with low coronary ostia distance, and in patients with an existing valve prosthesis, who may need a new valve prosthesis inside the existing valve prosthesis (valve-in-valve application). The support frame and the valve anchor can thus expand into contact with the aortic valve 304, exerting a chronic outward force against the native valve leaflets 306 and aortic valve annulus 320. Thereafter, the prosthetic valve leaflets of the prosthesis 100 can begin to function in the manner desired and provide the same operation as a native valve.

According to some embodiments, the present disclosure also provides a handle actuator that can be used to control the operation of the presently disclosed delivery device and allow a clinician to reliably and accurately control the delivery of the valve prosthesis. FIG. 1 illustrates features and operation of the handle actuator, according to some embodiments, for delivering a valve prosthesis using a handle actuator 500.

FIG. 1 illustrates the handle actuator 500, which can control one or more functions of a delivery device (e.g., the delivery device 200 discussed herein) for delivering of a valve prosthesis (e.g., the heart valve prosthesis 100 discussed herein). The handle actuator 500 can comprise a plurality of actuators or movable elements, such as knobs or buttons. The movable elements can permit a clinician to control one or more operations of the delivery device 200. The handle actuator 500 can comprise a control handle 510 having a longitudinal axis 512. The handle actuator 500 may be also referred to as a control unit. In some embodiments, the handle actuator 500 may be coupled to the second core member 222 (shown, e.g., in FIGS. 3 and 5). The control handle 510 can support the actuators and be held by the clinician during the procedure.

In some embodiments, as illustrated in FIG. 1, the handle actuator 500 can comprise a first movable element 520, a second movable element 522, a third movable element 524, and a fourth movable element 526. The first movable element 520 can be used to steer the delivery device 200, the second movable element 522 can be used to release the valve anchor, the third movable element 524 can be used to release nosecone or valve frame, and the fourth movable element 526 can be used as a nose cone toggle lock. The first movable element 520, the second movable element 522, the third movable element 524, and the fourth movable element 526 may be also referred to as the first control element 520, the second control element 522, the third control element 524, and the fourth control element 526.

Optionally, in some embodiments, one or more of the movable elements, such as the second movable element 522 and/or the third movable element 524, can include a button or slider safety switch 529 that prevent the unintentional rotation of the moveable elements. The safety switch 529 can be configured as resilient button or slider mechanisms that can be actuated to release a lock that provides resistance to rotational or translational movement of the respective movable element. In some embodiments, the movable elements can have a raised feature that provides a visual indication of rotation and facilitates tactile engagement and actuation by the clinician. Other features of the handle actuator 500 and methods for operating the handle actuator 500 are discussed and illustrated in FIGS. 13A-13H of U.S. Patent Application No. 62/781,537, filed on Dec. 18, 2018, the entirety of which is incorporated herein by reference.

Referring now to FIG. 2, a valve prosthesis 100 and components thereof are shown in various configurations. The valve prosthesis 100 can be delivered to a patient using a suitable delivery device, including embodiments of the delivery devices disclosed herein. The valve prosthesis 100 can comprise a support frame 102 and an anchoring component or valve anchor 104 to which the support frame 102 is movably connected, movably attached, flexibly connected, displaceably connected, linked, or coupled.

The valve prosthesis 100 can be configured such that components of the valve prosthesis 100 to be advanced in series while still being movably connected, movably attached, flexibly connected, displaceably connected, linked, or coupled to each other, thereby minimizing a passing profile or cross section of the delivery system. The interconnection of components of the valve prosthesis 100 can allow different degrees of motion and can be set into an engaged or retained position that provides a limited range of motion. In some embodiments, the engaged position can also provide a preset relative positioning of the components of the valve prosthesis 100 to facilitate proper placement and release of the valve prosthesis 100. Additionally, some embodiments can provide a clinician with a high degree of control and enhance the maneuverability of the valve prosthesis 100 when implanting the valve prosthesis 100 at the target location.

In some embodiments, the valve anchor 104 can be coupled to the support frame 102 when the support frame 102 is in the compact configuration prior to delivery and expansion. In some embodiments, the valve anchor 104 is not fixed to the support frame 102. Further, the valve anchor 104 can be separate from the support frame 102 or formed separately from and later coupled to the support frame 102. Thus, although a least a portion of the valve anchor 104, e.g., the anchoring leg, may be in contact with or otherwise reversibly attached or connected to the support frame 102, no part of the valve anchor 104 is fixed, e.g., welded or otherwise irreversibly adhered, to the support frame 102. Alternatively stated, the valve anchor 104, which may be in contact with or otherwise reversibly attached to the support frame 102, is not irreversibly fixed to the support frame 102.

Further, upon reaching the target location, the valve anchor 104 can be movably coupled to the support frame 102 in a manner that prevents the entire valve anchor 104 from being radially displaced from the support frame 102 when the valve anchor 104 is initially expanded. For example, portions of the valve anchor 104 can be radially displaced from the support frame during initial "landing" of the valve anchor 104 against the native valve structure at the target location. In some embodiments, the support frame 102 can be deployed or expanded within the native heart valve structure, and the valve anchor 104 can become sandwiched between the support frame and the native valve tissue, becoming at least partially, and possibly fully, immobilized. The valve anchor 104 can function to hold the expanded support frame 102 in place within the native valve structure.

Optionally, the support frame 102 may be referred to as a valve frame or valve support frame. FIG. 2 illustrates the support frame 102 aligned with and expanded within the valve anchor 104, in a configuration that is achieved when the prosthesis 100 is released and expanded within the native valve structure. The native valve structure includes the valve annulus or leaflets. This expanded configuration, serves to secure the valve prosthesis 100 within the native valve annulus by engaging the native valve structure. In some embodiments, the expanded configuration of the valve prosthesis 100 may reduce reliance on securing the valve prosthesis 100 with radial force exerted by the support frame 102 and the valve anchor 104 via the sandwiching or compression of the native valve leaflets between the support frame 102 and the valve anchor 104 of the valve prosthesis 100. Further, as discussed further herein, during implantation of the valve prosthesis 100, the support frame 102 and the valve anchor 104 can be movable relative to each other in expanded and/or compressed states in order to facilitate proper positioning of the prosthesis 100 relative to the native valve annulus and surrounding structures. Indeed, various advantages made possible by the prosthesis 100 and delivery device disclosed herein allow a clinician to achieve a higher degree of precision in placing the prosthesis 100, as well as making such increased precision easier to achieve.

Referring to FIG. 2, the support frame 102 can comprise an outer or external surface and defines a central orifice about a longitudinal axis 120. The longitudinal axis 120 corresponds to an inflow-outflow axis of the prosthesis 100. In some embodiments, the valve prosthesis 100 further comprises a plurality of prosthetic valve leaflets or cusps 106 that are coupled to the support frame 102. The support frame 102 can provide a structural support for the valve leaflets 106. The valve leaflets 106 can have surfaces defining a reversibly sealable opening for unidirectional flow of a liquid through the prosthesis 100. The prosthesis 100 can include three valve leaflets 106 for a tri-leaflet configuration. As appreciated, mono-leaflet, bi-leaflet, and/or multi-leaflet configurations are also possible. For example, the valve leaflets can be coupled to the support frame 102 to span and control fluid flow through the lumen of the prosthesis 100. The prosthetic leaflets 106 can comprise one or more synthetic materials, engineered biological tissues, biological valvular leaflet tissues, pericardial tissues, cross-linked pericardial tissues, aortic root tissue, chemically or biologically processed/treated tissue, or combinations thereof. In some embodiments, the pericardial tissue is selected from but not limited to the group consisting of bovine, equine, porcine, ovine, human tissue, or combinations thereof.

Furthermore, in some embodiments, the valve prosthesis 100 can comprise a sealing component or membrane 108 that can be attached to an inside surface, an outside surface, and/or enclose the support frame 102, such as by being laminated onto inner and outer surfaces of the support frame 102. Thus, the valve leaflets 106 can be coupled to the support frame 102 and/or the membrane 108. In some embodiments, the membrane 108 can restrict blood flow in areas around the valve leaflets 106 so that blood flow occurs only between the valve leaflets 106 through the lumen of the prosthesis 100, as in a healthy native heart valve.

The support frame 102 and/or the valve anchor 104 can comprise a braided frame, a wire frame, or a laser-cut frame (e.g., laser-cut tubular mesh), as shown in FIG. 2. In some embodiments, the support frame 102 and/or the valve anchor 104 can comprise a shape-memory metal, which can change shape at a designated temperature or temperature range or by inducing stress. Alternatively, the self-expanding frames can include those having a spring-bias. The material from which either the support frame 102 and/or the valve anchor 104 is fabricated can allow the support frame 102 and/or the valve anchor 104 to automatically expand to its functional size and shape when deployed but also allows the support frame 102 and/or the valve anchor 104 to be radially compressed to a smaller profile for delivery through the patient's vasculature. Examples of suitable materials for self-expanding components described herein (e.g., support frames, valve anchors, locking members) include, but are not limited to, medical-grade nickel titanium alloys, tantalum, platinum alloys, niobium alloys, cobalt alloys, alginate, or combinations thereof. Shape memory alloys having superelastic properties generally made from ratios of nickel and titanium, commonly known as Nitinol, are preferred materials. In some embodiments, self-expanding components described herein can include materials including, but not limited to shape memory plastics, polymers, and thermoplastic materials which are inert in the body. In an alternative embodiment, either the support frame 102 and/or the valve anchor 104 is not self-expanding, and may be expanded, for example, using a balloon catheter as is well known in the art. Examples of suitable materials for components described herein include, but are not limited to, stainless steel and titanium. Optionally, either the support frame 102 and/or the valve anchor 104 can comprise radiopaque materials to allow visualization under fluoroscopy or other imaging techniques.

Optionally, the support frame 102 can comprise one or more hooks 109 that can engage with tissue of the native valve annulus, the aortic root, or any other portion of the native valve when the support frame 102 is expanded within the native valve annulus. The hooks 109 can be engaged with the native valve annulus to secure the prosthesis 100 and mitigate any downstream or antegrade migration of the prosthesis 100 during operation.

The support frame 102 can comprise a first end portion 110 and a second end portion 112. The first end portion 110 can be positioned upstream of the second end portion 112 when the prosthesis 100 is released within the native valve annulus. As illustrated in FIG. 2, the first end portion 110 of the support frame 102 can be shaped as a generally flat end of a cylinder, where first apices 114 of the support frame 102 lie generally in a common plane, which can be oriented substantially perpendicular relative to a longitudinal axis 120 of the prosthesis 100. Further, the second end portion 112 can be shaped to include a series of peaks 130 and valleys 132, where second apices or minor peaks 136 of the support frame 102 collectively form contours of the peaks 130 and valleys 132. The peaks 130 and valleys 132 of the second end portion 112 can be positioned downstream of the first end portion 110 when the prosthesis is seated within the native valve annulus.

In accordance with some embodiments, the prosthetic leaflets 106 can be coupled relative to the support frame 102 at locations circumferentially aligned with the peaks 130 of the second end portion 112, as shown in FIG. 2. In some embodiments, the prosthetic leaflets 106 can be coupled to the membrane 108 using ultra-high molecular weight polyethylene sutures. This unique configuration can advantageously enable the prosthesis 100 to more fully approximate the native valve structures, permit a more natural blood flow without limiting or otherwise constraining movement of the valve leaflets 106, and more seamlessly integrate with surrounding architecture of the heart. In some embodiments, the prosthetic leaflets 106 can comprise features, including, but not limited to, planar features, flat features, three-dimensional features, Bézier curves, or other suitable shapes. Optionally, the prosthetic leaflets 106 can be shaped through fixation on a leaflet-shaped mandrel.

The valve anchor 104 can comprise at least one U-shaped member, valve clasper, sinus locator, valve positioner, or valve hanger 140 that extends about a longitudinal axis of the valve anchor 104. As illustrated in FIG. 2, the valve anchor 104 can comprise a plurality of lobes or U-shaped members 140, such as three U-shaped members 140, but can have fewer or more. In some embodiments, U-shaped members 140 can be configured to engage with or fit inside the posterior aortic sinus, the left aortic sinus, and the right aortic sinus of a native aortic valve. The U-shaped members 140 can each have a peak portion 142 and a base portion 144. The U-shaped members 140 can each comprise first and second legs 146, 148. The first and second legs 146, 148 of the adjacent U-shaped members 140 can be interconnected at the peak portions 142 thereof. Further, the U-shaped members 140 can comprise shapes other than a U-shape, such as a wave-shape, V-shape, W-shape, or zig-zag. Optionally, multiple valve anchors 104 can each comprise one or more U-shaped members 140, wherein the multiple valve anchors 104 cooperatively engage with the aortic sinus to anchor the valve prosthesis as described herein.

The valve prosthesis 100 can include a link mechanism that interconnects the support frame 102 to the valve anchor 104. The link mechanism can comprise a single, continuous strand of material or multiple, independent strands of material that interconnects the support frame 102 to the valve anchor 104. Further, the link mechanism can attach in a sliding, engaged, or fixed manner to one or more locations on the support frame 102 and/or on the valve anchor 104.

In accordance with some embodiments, the valve anchor 104 may optionally define one or more engagement areas in one or more portions of the valve anchor 104, where a link mechanism may engage with the one or more engagement areas to restrict relative motion between the support frame 102 and the valve anchor 104.

For example, at the interconnection of the respective peak portions, the valve anchor 104 can define an engagement area 150. The engagement area 150 may also be referred to as a peak portion engagement area.

As illustrated in FIG. 2, the support frame 102 can be flexibly coupled to the valve anchor 104 via one or more tethering components or link mechanisms 160. The link mechanism 160 can be coupled to the support frame 102 and to the valve anchor 104, permitting relative movement between the support frame 102 and the valve anchor 104. However, the link mechanism 160 can be configured to limit relative movement between the support frame 102 and to the valve anchor 104. In some embodiments, the engagement area 150 of the valve anchor 104 can be used to further restrict relative motion of the support frame 102 with respect to the valve anchor 104 when the link mechanism 160 is engaged in the engagement area 150, as discussed herein.

The valve anchor 104 can thus be coupled to the support frame 102 to permit the valve anchor 104 to be moved axially or longitudinally relative to the support frame 102 while still remaining coupled to the support frame 102. This advantageous feature of some embodiments can allow a clinician to independently position the valve anchor 104 relative to the support frame 102. For example, in a transcatheter aortic valve replacement, the clinician can independently position the valve anchor 104 in order to fit the base portions 144 of the valve anchor 104 into the aortic sinus. Portions of the of aortic sinus may include the posterior aortic sinus, the left aortic sinus, and/or the right aortic sinus, of a native aortic valve. In some embodiments, the valve anchor 104 can rotate to be aligned in the respective aortic sinuses. In some embodiments, the interconnection of the valve anchor 104 to the support frame 102 can allow the valve anchor 104 to self-rotate to be aligned in the aortic sinus. Thereafter, with the valve anchor 104 "landed" in the respective aortic sinuses, the interconnection of the valve anchor 104 to the support frame 102 further enables the support frame 102 to translated along the longitudinal axis 120 of the valve prosthesis 100. In some embodiments, during the delivery procedure, the valve anchor 104 can be moved at least axially from a proximal position relative to the support frame 102, to a distal position relative to the support frame 102, or from either of such positions to a position in which the support frame 102 at least partially longitudinally overlaps with or is concentric within the valve anchor 104. A range of various positions are illustrated, for example, in FIGS. 11A-11F of U.S. Patent Application No. 62/781,537, filed on Dec. 18, 2018, the entirety of which is incorporated herein by reference.

For example, when the support frame 102 is nested within the valve anchor 104, as shown in FIG. 2, the base portions 144 of the valve anchor 104 can be longitudinally spaced apart from first end portion 110 of the support frame 102 along the longitudinal axis 120 at a distance which is about 10% to about 100%, about 25% to about 75%, about 33% to about 100%, about 33% to about 66%, about 25% to about 75%, about 50% to about 75%, or about 60% to about 70% of a length of the support frame 102. In some embodiments, the support frame 102 can be contained or otherwise fully overlapping the valve anchor 104. In some embodiments, the support frame 102 can have minimal or no overlap with the valve anchor 104. The support frame 102 can move along the longitudinal axis 120 to overlap the valve anchor 104 by about 10% to about 100%, about 25% to about 75%, about 33% to about 100%, about 33% to about 66%, about 25% to about 75%, or about 50% to about 75% of the length of the support frame 102. In accordance with some embodiments, the U-shaped members 140 of the valve anchor 104 can be in nested positions within the aortic sinuses, and the base portions 144 of the valve anchor 104 can be about longitudinally adjacent to, coplanar with, or spaced apart from the first end portion 110 of the support frame 102. For example, the valve anchor 104 can be in a nested position when at least one base portion 144 of the valve anchor 104 is in contact with or adjacent to the basal attachments of the native aortic valvar leaflets. Further, the first end portion 110 of the support frame 102 can be longitudinally adjacent to, coplanar with, or spaced apart from the native valve structure (or a virtual ring formed by the basal attachments of the native aortic valvar leaflets) or with the ventriculo-aortic junction.

The link mechanism 160 can allow rotational and longitudinal movement of the valve anchor 104 relative to the support frame 102. Thus, despite the presence of the link mechanism 160, the valve anchor 104 can move rotationally with respect to the support frame 102. Further, in some embodiments, the link mechanism 160 can be fixedly attached or coupled to the support frame 102 and fixedly or slidably attached to the valve anchor 104. When the support frame 102 is moved relative to the valve anchor 104, the link mechanism 160 can slide along the U-shaped members 140. In some embodiments, the U-shaped members 140 have a generally arcuate or convex shape (as illustrated with the U-shaped members of FIG. 2) that allows unrestricted movement of the link mechanism 160 along the geometry of the first and second legs 146, 148 of the U-shaped members 140. When the link mechanism 160 is allowed to slide along the first and second legs 146, 148 of the U-shaped members 140, the valve prosthesis 100 can be in a position referred to as a "slidable" state. In the slidable state, the range of longitudinal and/or rotational movement of the support frame 102 relative to the valve anchor 104 is variable and may be its greatest because the link mechanism 160 can move along the first and second legs 146, 148 of the U-shaped members 140.

In some embodiments, the link mechanism 160 can be fixedly attached or coupled to the support frame 102 and fixedly attached to the valve anchor 104. When the support frame 102 is moved relative to the valve anchor 104, the link mechanism 160 can stretch, flex, deform elastically and/or plastically. As the link mechanism 160 deforms, the range of longitudinal and/or rotational movement of the support frame 102 relative to the valve anchor 104 is variable as allowed by the deformation of the link mechanism 160.

In some embodiments, the link mechanism 160 can have multiple link members, where each link member is coupled to and intermittently spaced about a circumference of the support frame 102. Each link member may be slidably coupled to a respective one of the U-shaped members 140. Further, the link mechanism 160 can have multiple link members that are coupled together in an end-to-end manner. Moreover, the link mechanism 160 can have multiple link members that are individually coupled at one and to the support frame 102 and at another and to the valve anchor 104. Each of the link members can be slidable along the valve anchor 104, as disclosed similarly herein and not described again herein for brevity.

As noted above, however, the valve anchor 104 can also comprise engagement areas 150 that can engage with the link mechanism 160 in order to restrict relative motion between the support frame 102 and the valve anchor 104. The engagement areas 150 can include one or more local concavities or other geometric shapes that can engage or trap the link mechanism 160 once the link mechanism 160 passes into the engagement area 150. Various embodiments of engagement areas 150 can be used to permit the slidable link mechanism 160 to enter into the engagement area 150, but restrict the link mechanism 160 from exiting the engagement area 150, such as those disclosed in FIGS. 2A-2G of U.S. Patent Application No. 62/781,537, noted above.

Figure 3:
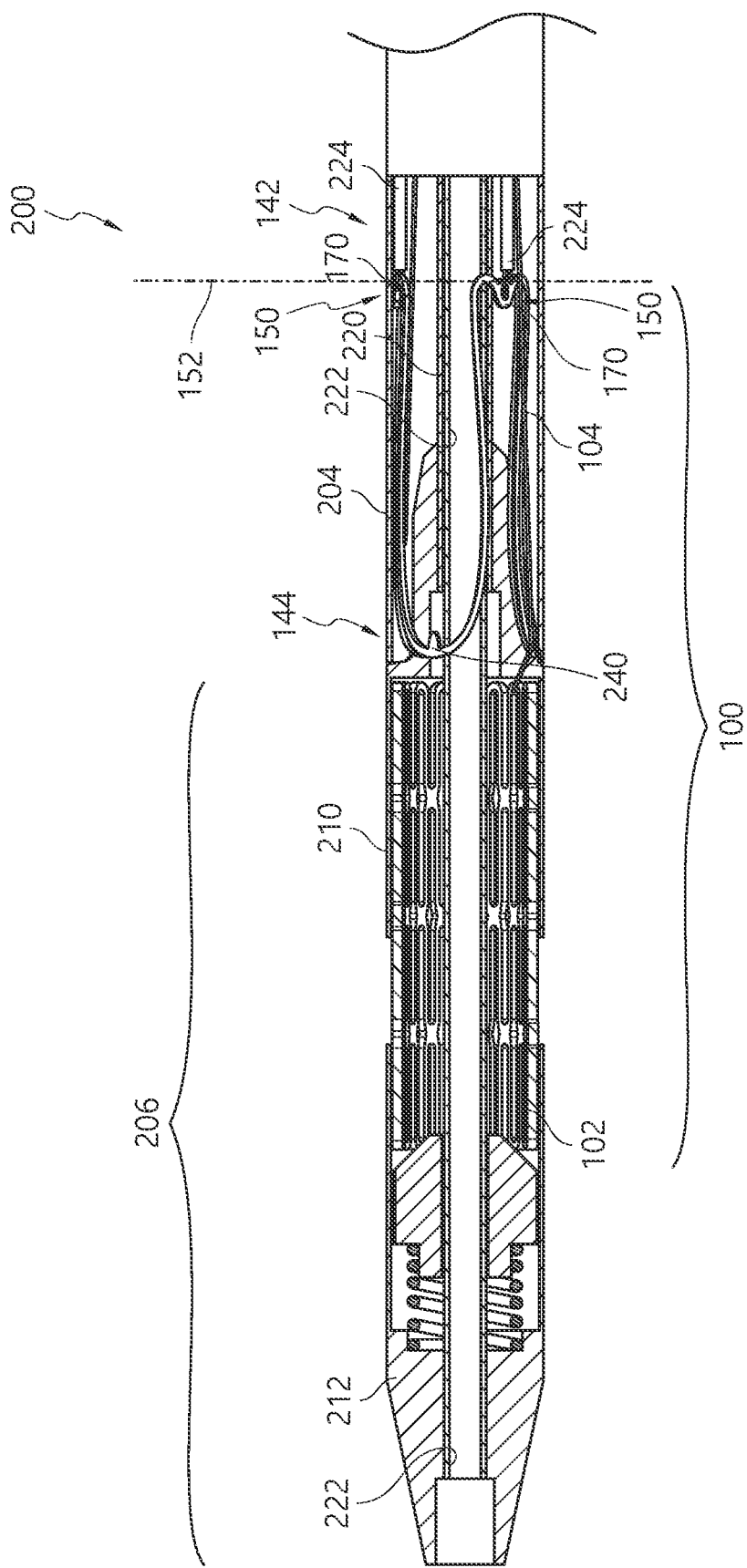
FIG. 3 is a side cross-sectional view of the valve prosthesis of FIG. 2 loaded onto a valve delivery device, according to some embodiments.

Referring now to FIG. 3, a side cross-sectional view is provided of the valve prosthesis 100 loaded onto the delivery device 200, according to some embodiments. Among the many features illustrated in FIG. 3, FIG. 3 shows that a proximal enclosure 210 of delivery device 200 can extend over both the valve anchor 104 and the support frame 102. Thus, in accordance with some embodiments, in the compressed or delivery configuration shown in FIG. 3, the link mechanism (not shown) can extend between the valve anchor 104 and the support frame 102 and be at least partially enclosed within the proximal enclosure 210 (depending on the attachment point of the link mechanism with the support frame 102 and the longitudinal extent of the proximal enclosure 210).

In addition, FIG. 3 illustrates that the valve anchor 104 can comprise a link motion limiter 240. The link motion limiter 240 can provide an enlarged profile of the wireframe structure of the valve anchor 104 so as to restrict or prevent motion of the link mechanism as the link mechanism slides along the U-shaped member of the valve anchor 104.

In alternative embodiments of the delivery device 200, the valve anchor 104 and the support frame 102 can both be enclosed within the proximal sheath component 204 prior to and during delivery prior to releasing the valve anchor 104. For example, in some embodiments, the valve anchor 104 can be distal to the support frame 102 wherein the valve anchor 104 is near the distal end of the proximal sheath component 204 and the support frame 102 can be approximately adjacent to the valve anchor 104 (in a serial configuration) and is proximal to the valve anchor 104. In some embodiments of the delivery device 200, the valve anchor 104 and the support frame 102 can both be enclosed within the proximal sheath component 204, with the support frame 102 near the distal end of the proximal sheath component 204 and the valve anchor 104 being approximately adjacent to the support frame 102 and proximal to the support frame 102.

Further, in alternative embodiments of the delivery device 200, the valve anchor 104 can be enclosed within the distal carrier assembly 206 and the support frame 102 can be enclosed within the proximal sheath component 204 prior to and during delivery of the valve prosthesis. For example, in some embodiments of the delivery device 200, both the valve anchor 104 and the support frame 102 can be enclosed within the distal carrier assembly 206 and the support frame 102 can be enclosed within the proximal sheath component 204 prior to and during delivery of the valve prosthesis. In this configuration, the valve anchor 104 and the support frame 102 can be approximately adjacent to one another (in a serial configuration) and the valve anchor 104 can be positioned proximal to the support frame 102. Other details of delivery devices and prostheses are provided in U.S. Patent Application No. 62/781,537, noted above and incorporated herein by reference.

In addition, FIG. 3 illustrates that an anchor retention component 170 can be used to engage the engagement areas 150 of the valve anchor 104 with the control member or a grasper 224 to facilitate movement and control of the positioning of the valve anchor 104 during delivery. As discussed with regard to FIGS. 7G-7I of U.S. Patent Application No. 62/781,537, noted above, this engagement can maintain the engagement areas 150 in a common plane 152, oriented generally perpendicular relative to the longitudinal axis of the delivery device 200.

Figure 4:
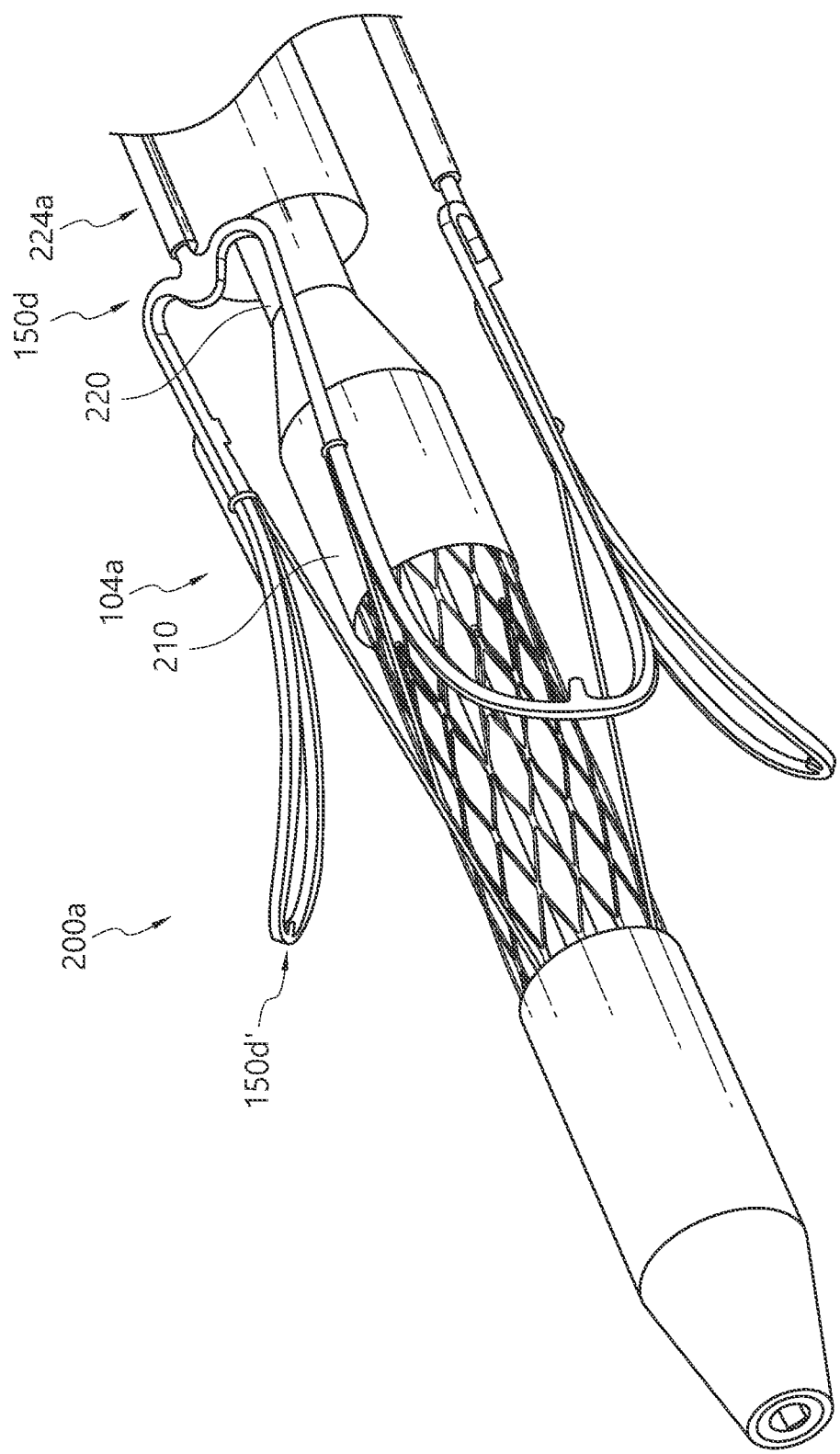
FIG. 4 is a perspective view the valve delivery device of FIG. 3 showing a grasper mechanism for engaging a valve anchor, according to some embodiments.

FIG. 4 illustrates aspects of the delivery device 200a, according to at least one embodiment. These figures do not illustrate all of the components of the delivery device that can be incorporated into an embodiment. However, the features illustrated in these figures can be incorporated into embodiments of the delivery device to facilitate engagement with the valve anchor and/or facilitate delivery and control of the valve anchor during implantation and release of the valve anchor at the target location.

For example, FIG. 4 illustrates an embodiment of a delivery device 200a that comprises a grasper mechanism. The grasper mechanism can be used to securely couple a portion of the valve anchor with the delivery device to permit the clinician to control movement, operation, and deployment of the valve anchor. The grasper mechanism can engage one or more portions or structures of the valve anchor using a variety of coupling mechanisms, which can use attachment means including mechanical engagement, dissolvable structures, chemically reactive degradable structures, electrolytically degradable structures, and the like.

In some embodiments, the grasper mechanism can be a tubular grasper mechanism. The delivery device 200a, shown in FIG. 4, can comprise a grasper 224a that can engage with and control the longitudinal position of the valve anchor 104a. The grasper 224a of the delivery device 200a can comprise an engagement wire that is movable within a lumen of a tubular enclosure. The valve anchor 104a can be configured to comprise a clasper tang extending from an engagement area 150d or 150d' of the valve anchor 104a. The engagement wire can comprise a distal end portion that includes pins, ridges, or protrusions that can be coupled to the engagement structure of the clasper tang at the engagement area of the valve anchor 104a. When engaged together, the engagement wire and the clasper tang can be proximally drawn into the lumen of the tubular enclosure, which secures the engagement wire and the clasper tang relative to each other in both radial and longitudinal directions. However, when the engagement wire and the clasper tang are moved outside of the lumen of the tubular enclosure, the engagement wire and the clasper tang can be disengaged as the valve anchor 104a and the clasper tang expand radially, thereby disengaging the clasper tang from the engagement wire. These and other features are discussed in U.S. Patent Application No. 62/781,537, noted above and incorporated herein by reference.

During use, after the valve anchor has been released from within the proximal sheath and after the valve anchor and the valve frame have been released from the delivery device, the delivery device can be configured to be compactly reassembled and withdrawn into the introducer sheath in order to minimize any damage to the blood vessel through which the delivery device was advanced.

Figure 5A:
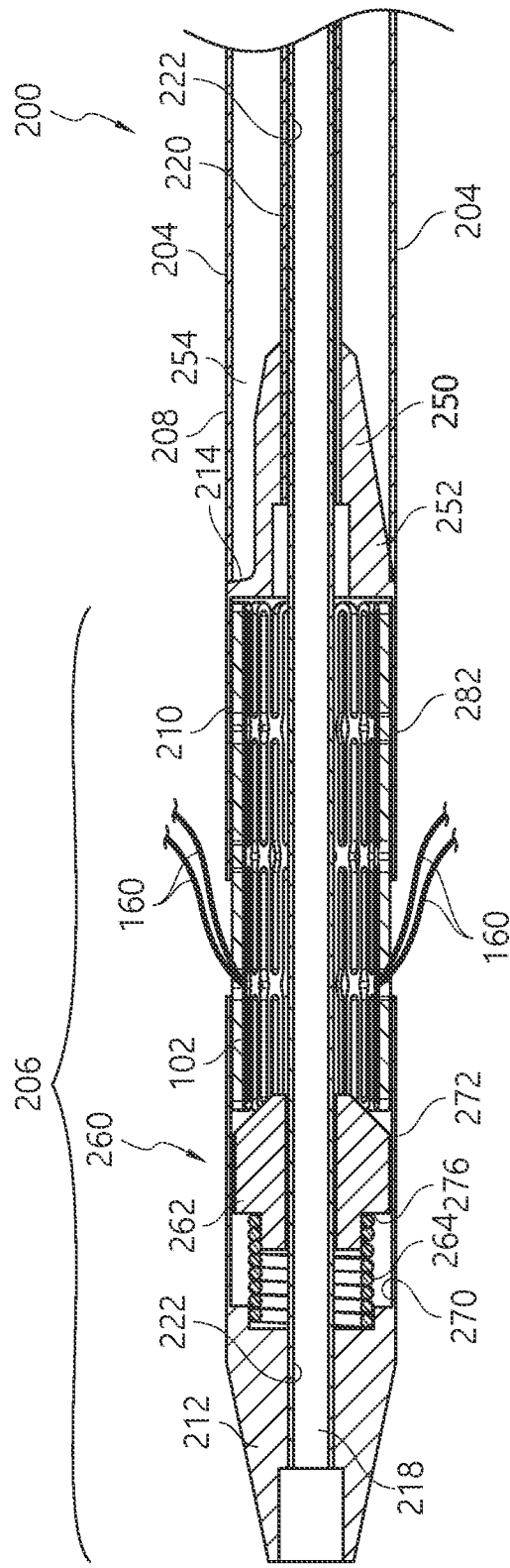
FIGS. 5A and 5B are side cross-sectional views illustrating operation of a distal carrier assembly of the valve delivery device of FIG. 3 with a nose cone protector, according to some embodiments.

For example, in at least one embodiment, as illustrated in FIG. 5A, the proximal enclosure 210 can comprise a proximal section 250 to facilitate realignment (e.g., radial realignment) of the distal end portion 208 of the proximal sheath component 204 with the proximal enclosure 210.

As illustrated in FIG. 5A, the proximal section 250 can be coupled to the core member 220. Further, the proximal section 250 can optionally be conical or tapered in a proximal direction and/or have circumferential nodes 252 and/or circumferential cavities 254 that can facilitate realignment of the proximal sheath component 204 relative to the proximal enclosure 210 along a longitudinal axis of the delivery device 200. The tapering of the proximal section 250 can allow the distal end portion 208 of the proximal sheath component 204 to smoothly advance distally over the proximal section 250, and the circumferential nodes 252 can contact an inner surface of the distal end portion 208 of the proximal sheath component 204 as the distal end portion 208 approaches the proximal abutment surface 214.

For example, as illustrated in FIG. 5A, the circumferential nodes 252 may gradually taper from the proximal abutment surface 214 in the proximal direction. With such a configuration, as the proximal sheath component 204 slides distally toward the proximal enclosure 210, the circumferential nodes 252 can advantageously guide the distal end portion 208 of the proximal sheath component 204 distally toward the proximal abutment surface 214 of the proximal enclosure 210 so that the outer surface of the proximal sheath component 204 is aligned with an outer surface of the proximal enclosure 210. Thus, the outer surfaces of the proximal enclosure 210 and the proximal sheath component 204 can provide a smooth outer profile for the delivery device 200 that can advantageously reduce the likelihood that the delivery device 200 catches or otherwise damages tissue within a body lumen as the delivery device 200 is moved therewithin.

Optionally, the proximal section 250 can comprise three circumferential nodes 252 and three circumferential cavities 254. The circumferential nodes 252 may extend proximally from the proximal abutment surface 214. The three circumferential cavities 254 can correspond to the number of U-shaped members of the valve anchor that are housed within the proximal sheath component 204 between the proximal sheath component 204 and the proximal section 250 of the proximal enclosure 210.

This advantageous feature of some embodiments can allow the distal enclosure 212 to be properly positioned along the delivery device 200 in order to ensure that distal enclosure 212 does not snag or become caught on any structure during retrieval of the delivery device 200.

Figure 5B:
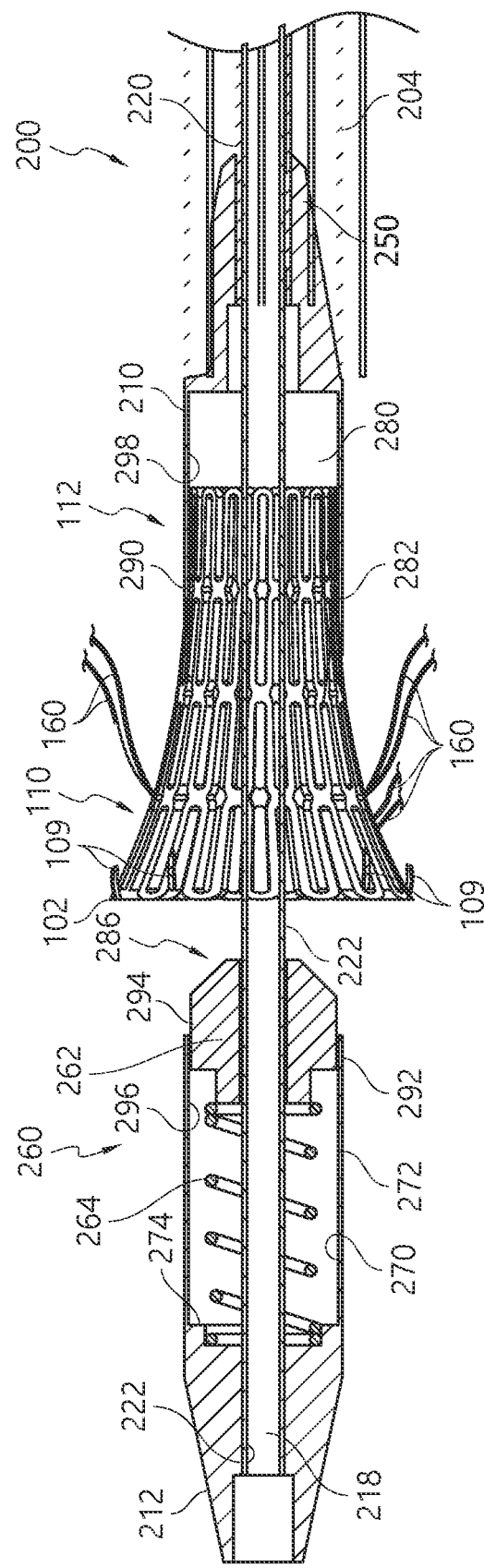

As also shown in FIGS. 5A and 5B, the proximal and distal enclosures 210, 212 can collectively house the support frame 102. The first and second core members 220, 222 can be actuated to separate the proximal and distal enclosures 210, 212, thereby permitting the support frame 102 to self-expand when in position within the valve anchor 104.

For example, by pushing or pulling the first core member 220, the second core member 222, and/or the proximal sheath component 204 relative to each other along the longitudinal axis of the delivery device 200, a clinician can control longitudinal movement of each of these components to permit the release of the support frame 102 and the valve anchor 104 of the valve prosthesis 100.

Further, in some embodiments, to facilitate delivery of the delivery device 200 to the target location, as shown in FIGS. 5A and 5B, the second core member 222 can include a lumen 218 to permit the delivery device 200 to move along a guidewire, which can extend through the lumen 218 of the second core member 222.

FIGS. 5A and 5B further illustrate positions of the proximal and distal enclosures 210, 212 during the release of the support frame 102. After separating the proximal and distal enclosures 210, 212 from the position illustrated in FIG. 5A to the position illustrated in FIG. 5A, the first end portion 110 of the support frame 102 can begin to expand from the compressed configuration to an expanded configuration. In some embodiments, the support frame 102 can have one or more anchors 109 (see also FIG. 2) at its first end portion 110 that, when engaged with the native valve structure can supplement the outward expansive force (due to self-expansion of the support frame 102) and its resultant frictional engagement, to mitigate downstream migration of the support frame 102 relative to the native valve structure. Thus, by opening the first end portion 110 first (before the second end portion 112, and via relative movement of the proximal and distal enclosures 210, 212), the first end portion 110 can "flower" out to facilitate release of the support frame and/or to engage with the native anatomy, such as the valve structure itself, to secure a longitudinal position of the support frame 102 relative to the native valve structure. Thereafter, the second end portion 112 of the support frame 102 can be controlled and released to become disengaged and released from the proximal enclosure 210.

In some embodiments, the first end portion 110 and the second end portion 112 can open simultaneously, at the same or different rates. For example, in some embodiments, the first end portion 110 and the second end portion 112 can open simultaneously, but with the first end portion 110 opening at a faster rate than the second end portion 112.

Advantageously, the use of the proximal enclosure 210 and the distal enclosure 212 allows for greater control and enhanced operation of the support frame 102. For example, by controlling the position and rate of separation of the proximal enclosure 210 and the distal enclosure 212, the opening of the support frame 102 at both the first end portion 110 and the second end portion 112 can be controlled. Further, by controlling the movement of the distal enclosure 212, the timing and rate of opening of the first end portion 110 can be controlled relative to the timing and rate of opening of the second end portion 112 (which may be controlled by the movement of the proximal enclosure 210).

Additionally and advantageously, by having separate proximal and distal enclosures 210, 212, the delivery device 200 may experience reduced frictional forces and minimize travel of the enclosures 210, 212 relative to the support frame 102.

In particular, in accordance with some embodiments, the distal carrier assembly 206 can comprise a plunger mechanism 260 that can facilitate expansion of the support frame 102. The plunger mechanism 260 can expand from a compressed state (shown in FIG. 5A) to an extended state (shown in FIG. 5A). The plunger mechanism 260 can be biased by a spring or other device in order to move automatically from the compressed state to the extended state. However, the plunger mechanism 260 can also be manually actuated by the clinician in some embodiments.

As illustrated, the plunger mechanism 260 can comprise a plunger head 262 and a biasing means 264. The plunger head 262 can comprise a conical or tapered proximal portion 286. The conical proximal portion 286 can be configured to not contact only the first end portion of the support frame 102 during delivery, but can also help center a distal end portion 290 of the tubular portion 282 of the proximal enclosure 210 relative to a longitudinal axis of the delivery device 200 and help align the distal end portion 290 with a proximal end portion 292 of the tubular portion 272 of the distal enclosure 212. The plunger head 262 can also comprise an outer circumferential surface 294 that can contact not only an inner surface 296 of the tubular portion 272, but can also contact an inner surface 298 of the tubular portion 282 when the tubular portion 282 is distally advanced over the conical proximal portion 286 of the plunger head 262.

Further, the plunger mechanism 260 can be housed within a distal lumen 270 of a tubular portion 272 of the distal enclosure 212. For example, the biasing means 264 may be a spring. The biasing means 264 can be interposed between an interior structure or wall 274 of the distal lumen 270 and a distal surface or structure 276 of the plunger head 262. The plunger head 262 can move proximally within the distal lumen 270 in order to continue to exert a proximally oriented force on the first end portion 110 of the support frame 102 until the support frame 102 exits the distal lumen 270. Thereafter, in accordance with some embodiments, the support frame 102 can self-expand until the second end portion 112 is pulled out of a proximal lumen 280 of a tubular portion 282 of the proximal enclosure 210 as the support frame 102 continues to expand. The expanded state of the support frame 102 is illustrated in FIGS. 1 and 2, discussed above.

According to some embodiments, the present disclosure optionally provides a membrane that can be used with the presently disclosed valve prosthesis to reduce the diameter of the support frame in a compressed configuration. FIGS. 6-11 illustrate aspects of the membrane 608 described herein.

Figure 6:
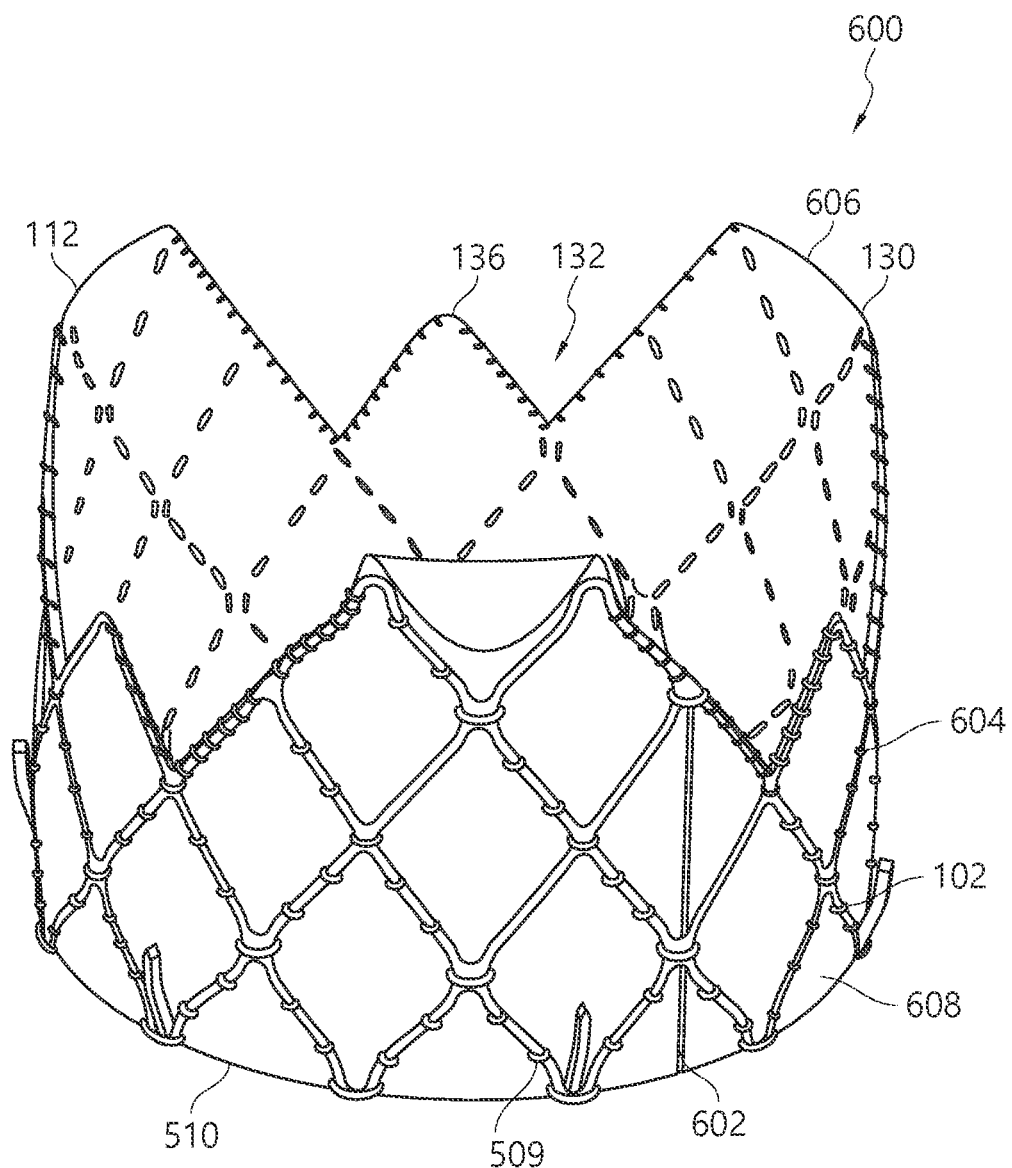
FIG. 6 shows a frame component of a valve prosthesis, according to some embodiments.

FIG. 6 illustrates a support frame 102 of a valve prosthesis 600 with a membrane 608 coupled thereto, according to some embodiments. In the embodiment shown in FIG. 6, the membrane 608 is positioned or disposed within a lumen or against an inner surface of the expanded support frame 102. As previously described, in some embodiments, the membrane 608 can serve as a sealing component and can be attached to the inside surface, the outside surface, and/or enclose the support frame 102.

In some embodiments, the membrane 608 can be affixed or otherwise attached to the support frame 102 via a plurality of sutures 604. The sutures 604 can attach the membrane 608 to the wire structure of the support frame 102 by passing through the membrane 608 and wrapping around portions of the support frame 102. In the illustrated embodiment of FIG. 6, the sutures 604 can be closely spaced (e.g., 2-4 sutures 604 per side of a parallelogram cell or diamond-shaped cell of the support frame 102) to create a tight seal between the membrane 608 and the support frame 102.

In some embodiments, the lateral ends of the membrane 608 can be attached at a seam 602 to form a generally cylindrical shape. As illustrated in FIG. 6, axial ends of the membrane 608 can be wrapped around the ends of the support frame 102 at the first end portion 110 and/or the second end portion 112. In some embodiments, the axial ends of the membrane 608 can wrap around the first end portion 110 and/or the second end portion 112 to at least partially cover both the inside surface and the outside surface of the support frame 102. For example, the peaks 606 of the membrane 608 can be wrapped over the peaks 130 of the second end 112 of the support frame 102. Advantageously, by wrapping the axial ends of the membrane 608 around the first and/or second ends 110, 112, the valve prosthesis 600 can be better sealed against the native heart valve. Further, the sutures 604 can be more densely spaced along the axial ends of the membrane 608 than where the membrane 608 is coupled to the support frame 102 intermediate the axial ends of the membrane 608.

As previously described, valve leaflets can be coupled to the membrane 608. In some embodiments, the membrane 608 can restrict blood flow in areas around the valve leaflets so that blood flow occurs only between the valve leaflets through the lumen of the prosthesis 600, as in a healthy native heart valve.

In some embodiments, at the second end portion 112, an axial end of the membrane 608 can be shaped to cover the major peaks 130 and valleys 132 of the second end 112. In some embodiments, the membrane 608 can be shaped to cover the second apices or minor peaks 136 within the valleys 132 between the major peaks 130. Advantageously, the configuration of the minor peaks 136 between the major peaks 130 can allow improved access to and prevent obstructions of the coronary ostia compared to prior art valve prostheses.

Figure 7A:
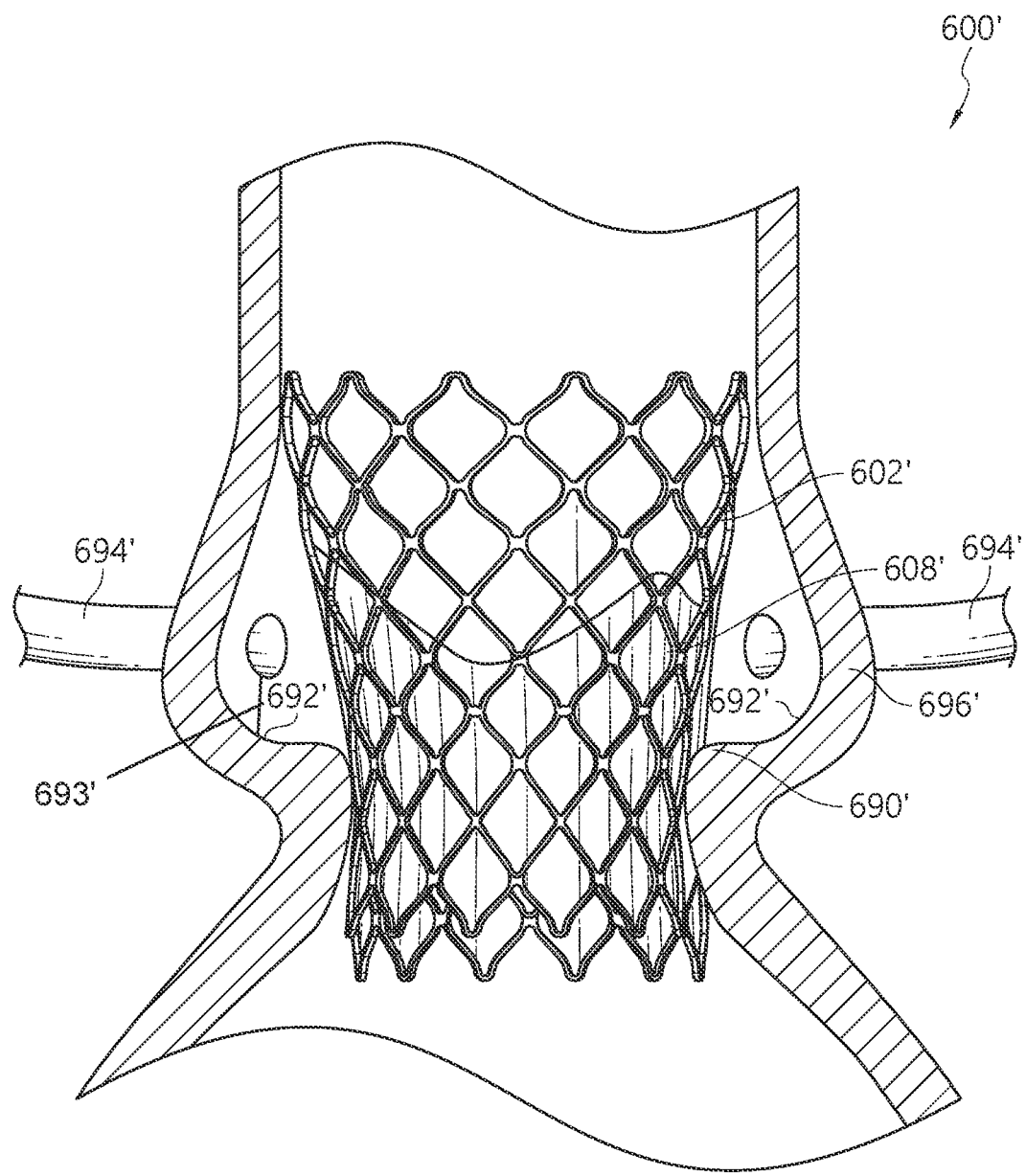
FIG. 7A shows a prior art valve prosthesis and its typical blockage of coronary ostia.

For example, referring to FIG. 7A, a prior art valve prosthesis 600' is shown within an aorta 696'. The support frame 602' is disposed within the aortic valve annulus 692'. As shown, the support frame 602' and membrane 608' may block or obstruct the coronary ostia 694' disposed a distance 693' away from the valve annulus 692' due to the geometry of the support frame 602' and the membrane 608'.

Figure 7B:
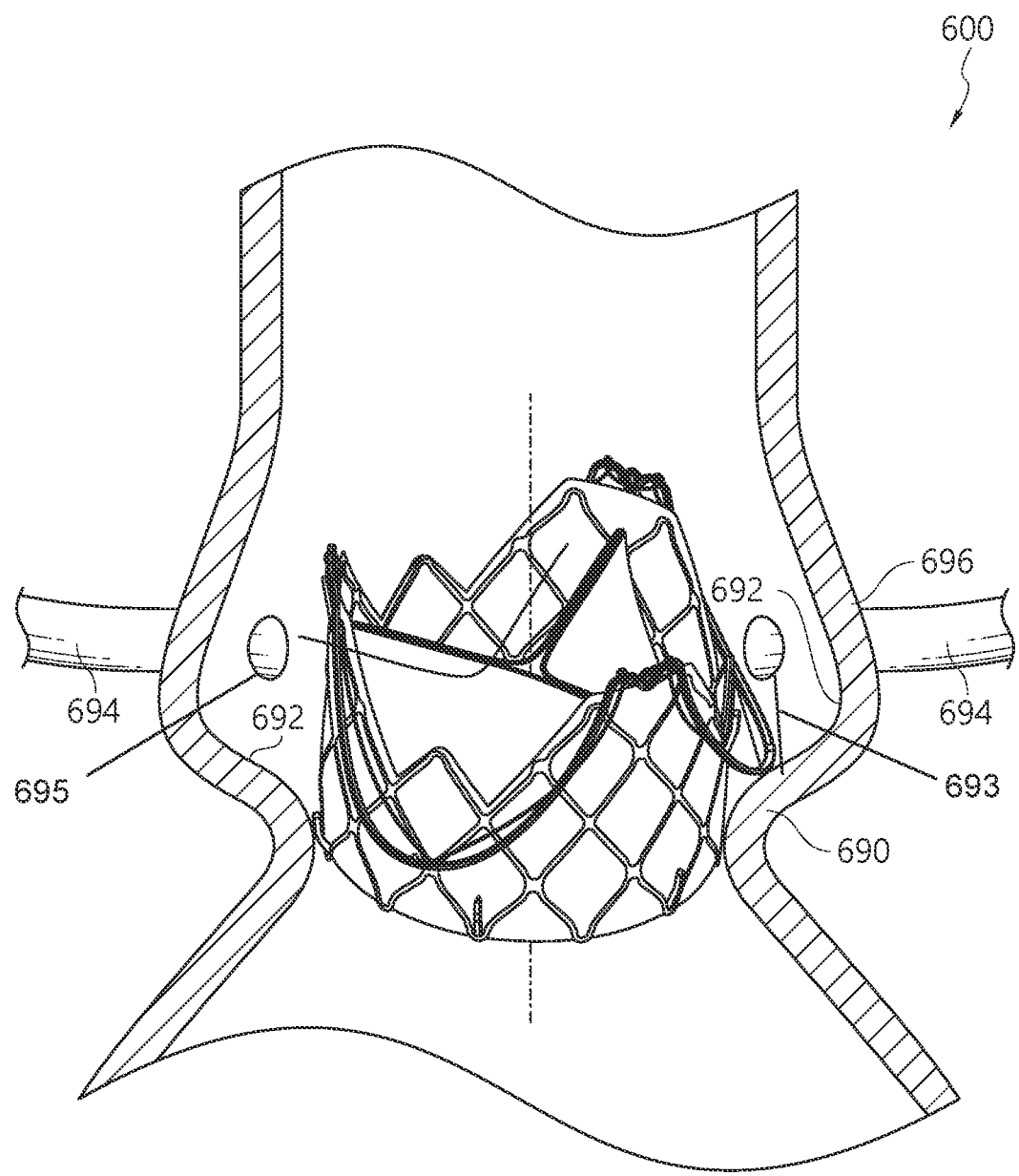
FIG. 7B shows the valve prosthesis of FIG. 6 positioned relative to a native valve structure, which can advantageously permit blood flow through one or more coronary ostia, according to some embodiments.

In contrast, FIG. 7B shows an embodiment of the valve prosthesis 600 that advantageously permits blood flow to adjacent coronary ostia 694. As discussed above, and as shown in FIG. 7B, the difference in height between the major peaks 130 and the minor peaks 136 of the valve prosthesis 600 facilitates access to the coronary ostia 694 while allowing for desired operation of the valve prosthesis 600.

In some embodiments, the minor peaks 136 of the valve prosthesis 600 can be low enough to allow a variety of sizes and locations of the coronary ostia 694 with respect to the native valve annulus 692 location of a patient. Advantageously, in some embodiments, the minor peaks 136 of the valve prosthesis 600 allow for access to coronary ostia 694 that are less than 10 mm, less than 8 mm, or less than 6 mm in coronary ostia height, which are typically excluded by conventional available prostheses. In some embodiments, the minor peaks 136, and optionally along with one or more other features described herein, allow for access to coronary ostia 694 that are disposed at a lower axial distance 693 relative to the valve annulus 692. For example, the minor peaks 136 can allow for access to coronary ostia 694 disposed at a coronary ostia height or lower axial distance 693 of less than 6 mm between the inferior edge of the coronary artery ostium 694 and the aortic annular plane. Furthermore, in some embodiments, the valve prosthesis 600 can be arranged to be disposed lower in the valve annulus 692 to allow greater access to the coronary ostia 694. By providing minor peaks 136 between the major peaks 130 of the valve prosthesis 600, and optionally used with one or more other features discussed herein, access to the coronary ostia 694 is preserved allowing for future procedures that may require access to the coronary ostia 694, such as coronary stenting.

Figure 8:
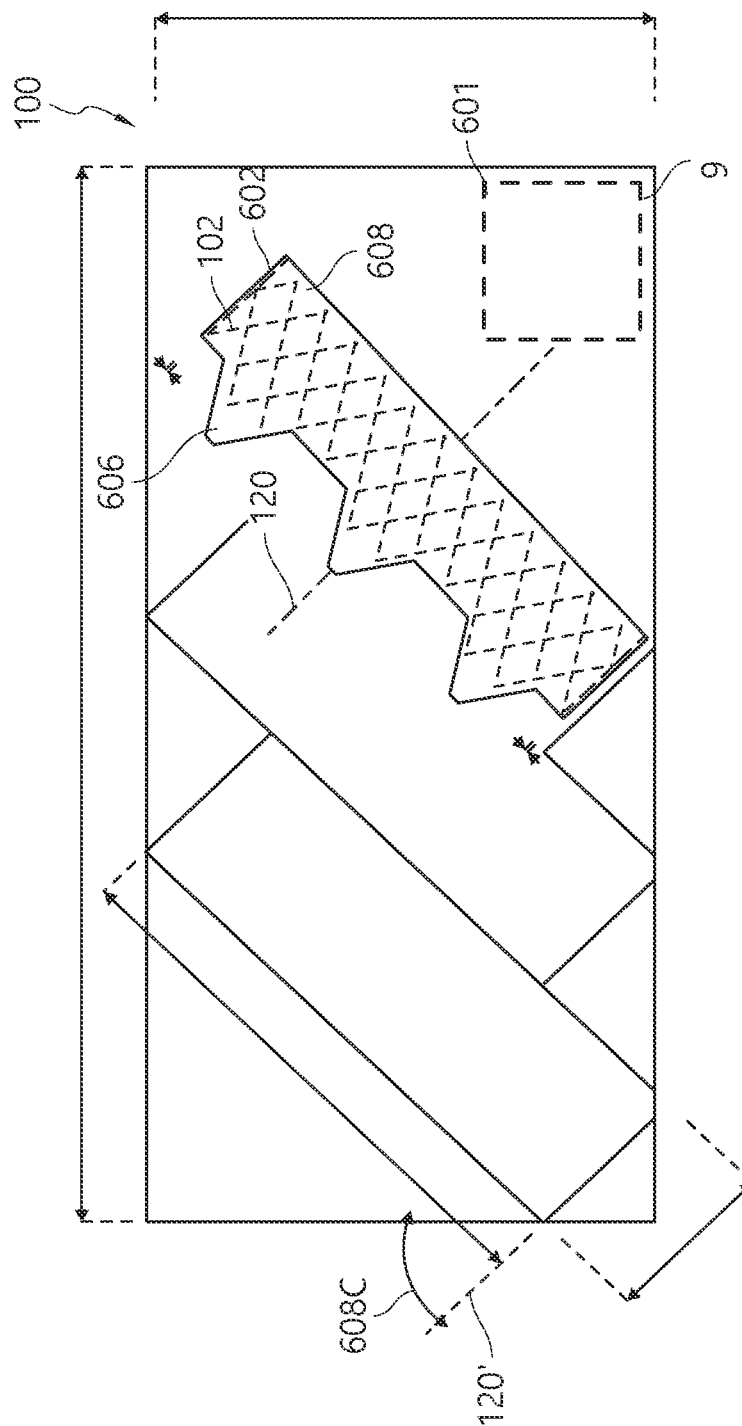
FIG. 8 illustrates aspects of a method for forming the membrane of the valve prosthesis, according to some embodiments.
Figure 9:
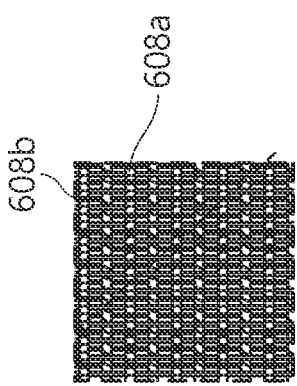
FIG. 9 is an enlarged view of a portion of the membrane fabric of FIG. 8.

FIG. 8 illustrates a method of forming or manufacturing the membrane for use with the valve prosthesis, which may be a portion of the method of forming the valve prosthesis. In some embodiments, one or more membranes 608 can be cut from a membrane fabric 601. The membrane fabric 601 can be a fabric formed from woven fiber, such as woven polyester. As shown in FIG. 9, the membrane fabric 601 is woven together with fibers in a warp direction 608a and a weft direction 608b that are oriented transverse, and in some cases, perpendicular, relative to each other. In some embodiments, a fabric may resist stretching in the warp and weft directions 608a, 608b while allowing stretching and compliance in directions oblique to or biased from the warp and weft directions 608a, 608b.

Referring back to FIG. 8, one or more membranes 608 can be cut from the membrane fabric 601 using templates that are generally in the shape of the membranes 608. One or more templates can be placed on the membrane fabric 601 to cut out the membranes 608. While the membrane 608 is shown in a flat orientation in FIG. 8, the support frame 102 and the projected longitudinal axis 120 thereof is shown for reference.

The templates can be oriented at an angle relative to the membrane fabric 601. A bias angle 608c can be defined between the edge of the membrane fabric 601 and the projected longitudinal axis 120. For reference, the bias angle 608c is shown between the edge of the membrane fabric 601 and an offset axis 120' that is parallel to the longitudinal axis 120. As discussed further below, the bias angle 608c can be from about 30 degrees to about 60 degrees, such as about 35 degrees, about 40 degrees, about 45 degrees, about 50 degrees, or about 55 degrees.

By orientating the templates at a bias angle 608c relative to the membrane fabric 601, the resulting membrane 608 is cut on the bias with the bias angle 608c with respect to the warp and weft directions 608a, 608b of the membrane fabric 601. In some embodiments, the membrane 608 can be cut at the bias angle 608c by spiral wrapping the membrane fabric onto the support frame and cutting the membrane fabric 601.

Figure 10:
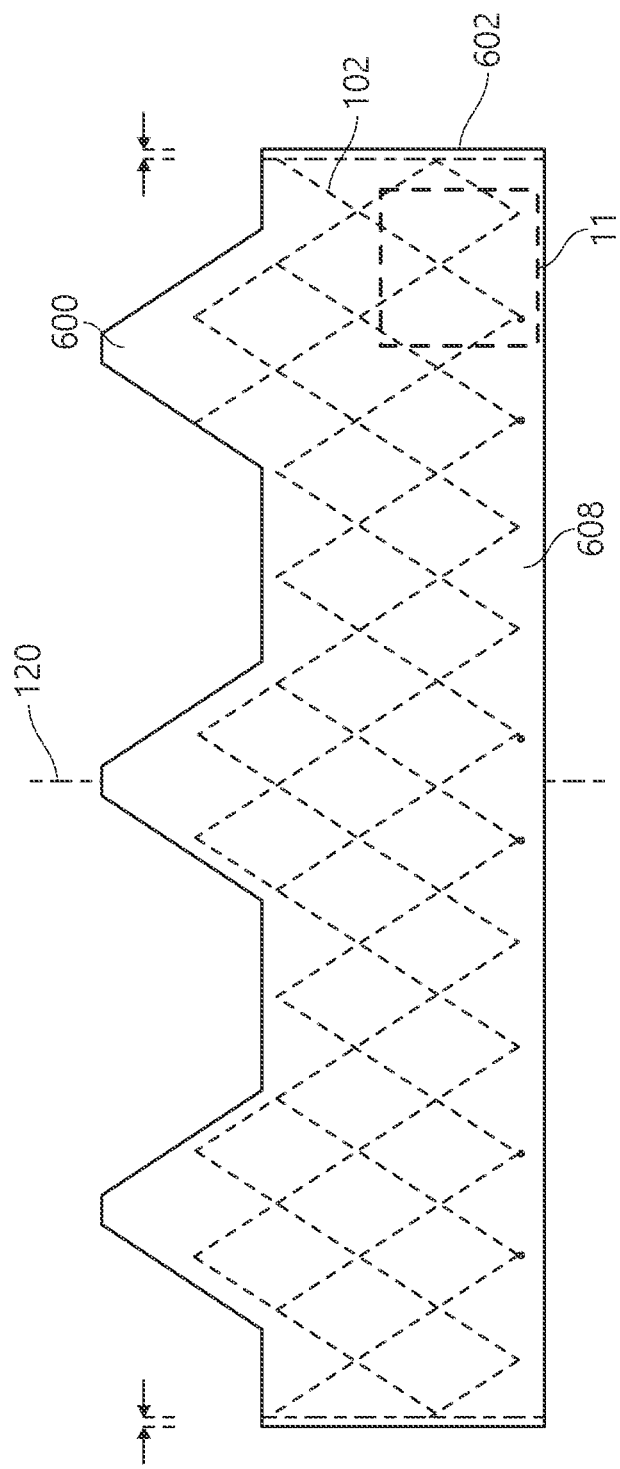
FIG. 10 illustrates the membrane of the valve prosthesis of FIG. 6, according to some embodiments.

FIG. 10 illustrates a resultant membrane 608 manufactured using the process shown in FIGS. 8 and 9. In the depicted embodiment, the warp and weft of the fabric of the membrane 608 is oriented at a bias or diagonal with respect to the direction of a longitudinal axis of the prosthesis. In some embodiments, the bias angle of the membrane 608 can be generally oriented such that the warp or the weft of the material is aligned with expandable elements (e.g., the cells, parallelogram cells, or diamond-shaped cells) of the support frame 102. Advantageously, in some embodiments, the membrane 608 may have increased conformability and may not resist movement or expansion of the support frame 102, thereby reducing stress and bunching of the membrane 608 when the membrane 608 and prosthesis are in a compressed configuration. In some embodiments, the reduction of stress on both the membrane 608 and the support frame 102 can facilitate both assembly and loading of the valve prosthesis.

Indeed, development of some embodiments of the prosthesis has shown that the unique orientation and configuration of the membrane 608 described herein can permit the membrane 608 to more easily radially compress and axially elongate in tandem with the support frame 102, thus permitting the membrane 608 and the support frame 102 to operate as a single unit, in some embodiments. Similarly, in some embodiments, by orientating the membrane 608 along a bias angle, the membrane 608 can more readily elongate along longitudinal axis 120 to obtain a smaller cross-sectional profile, which can prevent flaring, bunching, or pleating, thereby minimizing the cross-sectional profile of the valve prosthesis in a compressed configuration.

Figure 11:
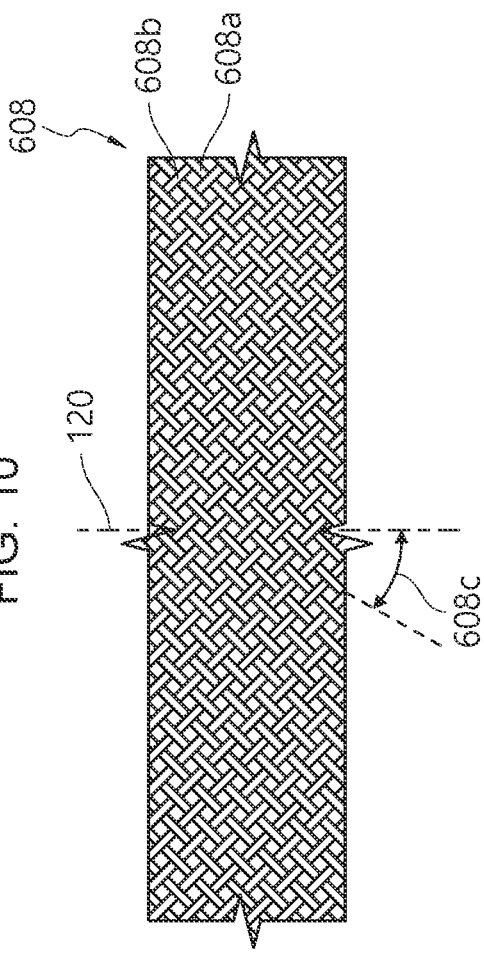
FIG. 11 is an enlarged view of a portion of the membrane of FIG. 10, according to some embodiments.

FIG. 11 is a plan view of the warp 608a and the weft 608b of the membrane 608 relative to the longitudinal axis 120 of the support frame 102. In some embodiments, the warp 608a and weft 608b of the woven membrane 608 can be oriented relative to the longitudinal axis 120 at a bias angle 608c between 0 and 90 degrees. In some embodiments, the woven membrane 608 can be oriented at a bias angle 608c between 15 and 75 degrees relative to the longitudinal axis 120. In some embodiments, the woven membrane 608 can be oriented at a bias angle 608c between 30 and 60 degrees relative to the longitudinal axis 120. In some embodiments, the woven membrane 608 can be oriented at a bias angle 608c of approximately 45 degrees relative to the longitudinal axis 120.

In some embodiments, the warp and weft of the woven membrane 108 can be oriented relative to the longitudinal axis at a bias angle between 0 and 90 degrees. In some embodiments, the woven membrane 108 can be oriented at a bias angle between about 15 and about 75 degrees relative to the longitudinal axis. In some embodiments, the woven membrane 108 can be oriented at a bias angle between about 30 degrees and about 60 degrees relative to the longitudinal axis. In some embodiments, the woven membrane 108 can be oriented at a bias angle of about 45 degrees relative to the longitudinal axis.

Illustration of Subject Technology as Clauses

Various examples of aspects of the disclosure are described as clause sets having numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A valve prosthesis comprising: a support frame comprising a plurality of cells arranged to define a bottom edge of the support frame, a plurality of major peak portions opposite the bottom edge, and at least one minor peak portion disposed longitudinally intermediate the bottom edge and the plurality of major peak portions; and a membrane attached to the support frame.

Clause 2. The valve prosthesis of Clause 1, wherein the membrane comprises a first end portion corresponding to the bottom edge of the support frame, a plurality of membrane major peak portions corresponding to the plurality major peak portions of the support frame, and at least one membrane minor peak portion corresponding to the at least one minor peak portion of the support frame.

Clause 3. The valve prosthesis of Clause 2, wherein one or more membrane major peak portions of the plurality of membrane major peak portions are wrapped around corresponding one or more major peak portions of the plurality of major peak portions of the support frame to cover a part of an inner surface and a part of an outer surface of the support frame at the corresponding one or more major peak portions of the support frame.

Clause 4. The valve prosthesis of Clause 3, wherein one or more membrane minor peak portions of the at least one membrane minor peak portion are wrapped around corresponding one or more minor peak portions of the at least one minor peak portion of the support frame to cover a part of an inner surface and a part of an outer surface of the support frame at the corresponding one or more minor peak portions of the support frame.

Clause 5. The valve prosthesis of any preceding Clause, wherein the at least one minor peak portion is disposed at a lower axial distance from the bottom edge compared to the plurality of major peak portions.

Clause 6. The valve prosthesis of any preceding Clause, wherein the membrane encloses the support frame with one or more openings along a longitudinal axis of the support frame.

Clause 7. The valve prosthesis of any preceding Clause, wherein the membrane is disposed within a lumen of the support frame to be attached to an inner surface of the support frame.

Clause 8. The valve prosthesis of any preceding Clause, wherein the membrane is laminated onto inner and outer surfaces of the support frame.

Clause 9. The valve prosthesis of any preceding Clause, wherein the membrane is attached to the support frame via a plurality of sutures.

Clause 10. The valve prosthesis of Clause 9, wherein the plurality of sutures are passed through the membrane and are wrapped around a plurality of portions of the support frame.

Clause 11. The valve prosthesis of Clause 9, wherein a first set of the plurality of sutures along a plurality of top portions corresponding to the plurality of major peak portions and the at least one minor peak portion of the support frame is more densely spaced than a second set of the plurality of sutures coupled to portions of the support frame intermediate the plurality of top portions and a plurality of base portions.

Clause 12. The valve prosthesis of any preceding Clause, wherein membrane fabric of the membrane is formed from woven fiber.

Clause 13. The valve prosthesis of Clause 12, wherein the membrane fabric is formed by weaving fibers in a warp direction and a weft direction that are oriented transverse relative to each other.

Clause 14. The valve prosthesis of Clause 13, wherein the membrane fabric resists stretching in the warp direction and the weft direction of the fibers.

Clause 15. The valve prosthesis of Clause 13, wherein the membrane fabric stretches in one or more directions oblique to the warp direction or the weft direction of the fibers.

Clause 16. The valve prosthesis of any preceding Clause, further comprising: a plurality of valve leaflets coupled to the membrane.

Clause 17. The valve prosthesis of Clause 16, wherein the membrane is coupled to the plurality of valve leaflets to restrict fluid flow around the plurality of valve leaflets and to direct the fluid flow to an area between the plurality of valve leaflets.

Clause 18. A method of manufacturing a membrane for a support frame of a valve prosthesis, the method comprising: creating a template on a membrane fabric in a shape of one or more membranes to be attached to a support frame of a valve prosthesis; orientating the template at a bias angle relative to the membrane fabric; and generating one or more membranes from the membrane fabric using the template.

Clause 19. The method of Clause 18, wherein the membrane fabric is formed from woven fiber.

Clause 20. The method of Clause 19, wherein the membrane fabric is formed by weaving fibers in a warp direction and a weft direction that are oriented transverse relative to each other.

Clause 21. The method of Clause 20, wherein the membrane fabric resists stretching in the warp direction and the weft direction of the fibers.

Clause 22. The method of Clause 20, wherein the membrane fabric stretches in one or more directions oblique to the warp direction or the weft direction of the fibers.

Clause 23. The method of Clause 18-22, wherein the bias angle is about 30 degrees to about 60 degrees.

Clause 24. A valve prosthesis, comprising: a support frame having a longitudinal axis; and a membrane coupled to the support frame, the membrane comprising: a plurality of first fibers arranged in a warp direction, and a plurality of second fibers arranged in a weft direction that is transverse relative to the warp direction, the plurality of first fibers and the plurality of second fibers being woven together, the warp and weft directions being oblique relative to the longitudinal axis of the support frame.

Clause 25. The valve prosthesis of Clause 24, wherein the warp and weft directions are aligned with expandable elements of the support frame, the expandable elements being expandable during a transition between a compressed configuration and an expanded configuration of the support frame.

Clause 26. A method of manufacturing a valve prosthesis, the method comprising: aligning a membrane along a support frame having a longitudinal axis, the membrane comprising: a plurality of first fibers arranged in a warp direction, and a plurality of second fibers arranged in a weft direction that is transverse relative to the warp direction, the plurality of first fibers and the plurality of second fibers being woven together, the warp and weft directions being oblique relative to the longitudinal axis of the support frame; and attaching the membrane to the support frame.

Clause 27. The method of Clause 26, wherein the membrane is attached to the support frame via a plurality of sutures, the plurality of sutures permitting movement of the membrane relative to the support frame when the membrane is attached to the support frame.

Clause 28. The method of Clause 27, wherein the support frame is made of a wire structure, and wherein the membrane is attached to the support frame by passing the plurality of sutures through the membrane and wrapping around a plurality of portions of the wire structure of the support frame.

Clause 29. The method of Clause 26-28, wherein the support frame includes one or more peak portions and one or more base portions, and the membrane includes one or more membrane peak portions corresponding to the one or more peak portions of the support frame and the one or more membrane base portions corresponding to the one or more base portions of the support frame.

Clause 30. The method of Clause 29, further comprising: wrapping the one or more membrane peak portions over the one or more peak portions of the support frame, respectively.

Clause 31. The method of Clause 26, further comprising: forming a cylindrical shape with the membrane by attaching one lateral end of the membrane to another lateral end of the membrane, the cylindrical shape corresponding to a shape of the support frame.

Clause 32. The method of Clause 26, wherein the warp and weft directions are aligned with expandable elements of the support frame, the expandable elements being expandable during a transition between a compressed configuration and an expanded configuration of the support frame.

Clause 33. A method for delivering a prosthetic heart valve prosthesis to a native valve structure of a patient at an implantation site, the method comprising: introducing the valve prosthesis into the patient at the implantation site, the valve prosthesis including a valve anchor and an expandable valve frame comprising a bottom edge, a plurality of major peak portions, and at least one minor peak portion disposed longitudinally intermediate the bottom edge and the plurality of major peak portions; permitting expansion of the valve anchor; distally urging a portion of the valve anchor into engagement with a native valve structure; permitting the valve anchor to expand against the native valve structure; rotating the valve frame to rotationally align the minor peak portion with an ostia at the implantation site; and permitting expansion of the valve frame within a lumen of the valve anchor.

Clause 34. The method of Clause 33, wherein the minor peak portion is disposed at a lower axial distance relative to the ostia.

Clause 35. The method of Clause 34, wherein the distally advancing the valve frame into the valve anchor comprises distally advancing the valve frame until further distal movement of the valve frame relative to the valve anchor is restricted by a link mechanism.

Clause 36. The method of Clause 33-35, wherein prior to the permitting expansion of the valve frame, the method further comprises distally advancing the valve frame into the valve anchor.

Further Considerations

In some embodiments, any of the clauses herein may depend from any one of the independent clauses or any one of the dependent clauses. In some embodiments, any of the clauses (e.g., dependent or independent clauses) may be combined with any other one or more clauses (e.g., dependent or independent clauses). In some embodiments, a claim may include some or all of the words (e.g., steps, operations, means or components) recited in a clause, a sentence, a phrase or a paragraph. In some embodiments, a claim may include some or all of the words recited in one or more clauses, sentences, phrases or paragraphs. In some embodiments, some of the words in each of the clauses, sentences, phrases or paragraphs may be removed. In some embodiments, additional words or elements may be added to a clause, a sentence, a phrase or a paragraph. In some embodiments, the subject technology may be implemented without utilizing some of the components, elements, functions or operations described herein. In some embodiments, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the term "distal" can denote a location or direction that is away from a point of interest, such as a control unit or region of the delivery system that will be used to deliver a valve prosthesis to a native valve annulus. Additionally, the term "proximal" can denote a location or direction that is closer to a point of interest, such as a control unit or region of the delivery system that will be used to deliver a valve prosthesis.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method of manufacturing a valve prosthesis, the method comprising:
   aligning a membrane along a support frame having a longitudinal axis, the membrane comprising:
      a plurality of first fibers arranged in a warp direction, and
      a plurality of second fibers arranged in a weft direction that is transverse relative to the warp direction, the plurality of first fibers and the plurality of second fibers being woven together, the warp and weft directions being oblique relative to the longitudinal axis of the support frame; and
   attaching the membrane to the support frame.

2. The method of claim 1, wherein the attaching comprises attaching the membrane to the support frame via a plurality of sutures, the plurality of sutures permitting movement of the membrane relative to the support frame when the membrane is attached to the support frame.

3. The method of claim 2, wherein the support frame is made of a wire structure, and wherein the attaching comprises passing the plurality of sutures through the membrane and wrapping around a plurality of portions of the wire structure of the support frame.

4. The method of claim 1, wherein the support frame includes one or more peak portions and one or more base portions, and the membrane includes one or more membrane peak portions corresponding to the one or more peak portions of the support frame and the one or more membrane base portions corresponding to the one or more base portions of the support frame.

5. The method of claim 4, further comprising wrapping the one or more membrane peak portions over the one or more peak portions of the support frame, respectively.

6. The method of claim 1, further comprising forming a cylindrical shape with the membrane by attaching one lateral end of the membrane to another lateral end of the membrane, the cylindrical shape corresponding to a shape of the support frame.

7. The method of claim 1, wherein the warp and weft directions are aligned with expandable elements of the support frame, the expandable elements being expandable during a transition between a compressed configuration and an expanded configuration of the support frame.

8. The method of claim 7, wherein the membrane resists stretching in the warp direction and the weft direction of the fibers.

9. The method of claim 7, wherein the membrane stretches in one or more directions oblique to the warp direction or the weft direction of the fibers.

10. The method of claim 1, wherein the aligning comprises aligning a first end portion of the membrane with the bottom edge of the support frame, aligning a plurality of membrane major peak portions of the membrane with the plurality major peak portions of the support frame, and aligning at least one membrane minor peak portion of the membrane with the at least one minor peak portion of the support frame.

11. The method of claim 10, wherein the attaching comprises wrapping one or more membrane major peak portions of the plurality of membrane major peak portions around corresponding one or more major peak portions of the plurality of major peak portions of the support frame to cover a part of an inner surface and a part of an outer surface of the support frame at the corresponding one or more major peak portions of the support frame.

12. The method of claim 11, wherein the attaching further comprises wrapping one or more membrane minor peak portions of the at least one membrane minor peak portion around corresponding one or more minor peak portions of the at least one minor peak portion of the support frame to cover a part of an inner surface and a part of an outer surface of the support frame at the corresponding one or more minor peak portions of the support frame.

13. The method of claim 1, wherein the warp direction is perpendicular to the weft direction.

14. A method of manufacturing a heart valve prosthesis that comprises coupling a woven membrane to a support frame of the heart valve prosthesis, and aligning warp and weft fibers of the membrane in warp and weft directions that are oblique relative to a longitudinal axis of the support frame.

15. The method of claim 14, wherein the coupling comprises attaching the membrane to the support frame via a plurality of sutures, the plurality of sutures permitting movement of the membrane relative to the support frame when the membrane is attached to the support frame.

16. The method of claim 15, wherein the support frame is made of a wire structure, and wherein the attaching comprises passing the plurality of sutures through the membrane and wrapping around a plurality of portions of the wire structure of the support frame.

17. The method of claim 14, wherein the support frame includes one or more peak portions and one or more base portions, and the membrane includes one or more membrane peak portions corresponding to the one or more peak portions of the support frame and the one or more membrane base portions corresponding to the one or more base portions of the support frame.

18. The method of claim 17, further comprising wrapping the one or more membrane peak portions over the one or more peak portions of the support frame, respectively.

19. The method of claim 14, further comprising forming a cylindrical shape with the membrane by attaching one lateral end of the membrane to another lateral end of the membrane, the cylindrical shape corresponding to a shape of the support frame.

20. The method of claim 14, wherein the warp and weft directions are aligned with expandable elements of the support frame, the expandable elements being expandable during a transition between a compressed configuration and an expanded configuration of the support frame.

* * * * *